US012383485B1

(12) United States Patent
Rosen

(10) Patent No.: US 12,383,485 B1
(45) Date of Patent: Aug. 12, 2025

(54) MULTI-COMPONENT NUTRITIONAL SUPPLEMENT FORMULATIONS AND TREATMENT REGIMEN

(71) Applicant: Gene S. Rosen, Miami, FL (US)

(72) Inventor: Gene S. Rosen, Miami, FL (US)

( * ) Notice: Subject to any disclaimer, the term of this patent is extended or adjusted under 35 U.S.C. 154(b) by 969 days.

(21) Appl. No.: 17/478,885

(22) Filed: Sep. 18, 2021

Related U.S. Application Data

(63) Continuation of application No. 17/220,520, filed on Apr. 1, 2021, now Pat. No. 11,369,558, which is a continuation-in-part of application No. 16/259,304, filed on Jan. 28, 2019, now Pat. No. 10,980,791.

(60) Provisional application No. 62/761,194, filed on Mar. 15, 2018, provisional application No. 62/709,659, filed on Jan. 26, 2018.

(51) Int. Cl.
| | |
|---|---|
| *A61K 8/65* | (2006.01) |
| *A61K 8/34* | (2006.01) |
| *A61K 8/46* | (2006.01) |
| *A61Q 3/00* | (2006.01) |
| *A61Q 19/00* | (2006.01) |
| *A61Q 19/08* | (2006.01) |

(52) U.S. Cl.
CPC ............... *A61K 8/65* (2013.01); *A61K 8/347* (2013.01); *A61K 8/46* (2013.01); *A61Q 3/00* (2013.01); *A61Q 19/001* (2013.01); *A61Q 19/08* (2013.01)

(58) Field of Classification Search
CPC . A61K 8/65; A61K 8/347; A61K 8/46; A61Q 3/00; A61Q 19/001; A61Q 19/08
USPC ........................................................ 514/18.8
See application file for complete search history.

(56) References Cited

U.S. PATENT DOCUMENTS

| | | | |
|---|---|---|---|
| 4,296,130 A | 10/1981 | Herschler | |
| 8,491,889 B1 | 7/2013 | Calton et al. | |
| 9,682,048 B1 * | 6/2017 | Rosen | A61K 31/7004 |
| 10,980,791 B1 | 4/2021 | Rosen | |
| 11,369,558 B1 | 6/2022 | Rosen | |
| 2004/0241256 A1 | 12/2004 | Ehrenpreis et al. | |
| 2008/0213401 A1 * | 9/2008 | Smith | A23L 33/105 424/722 |
| 2009/0312273 A1 * | 12/2009 | De La Torre | A61P 25/28 514/23 |
| 2011/0070315 A1 | 3/2011 | Taylor | |
| 2012/0263698 A1 | 10/2012 | Barber | |
| 2014/0142172 A1 | 5/2014 | Cole et al. | |
| 2017/0231888 A1 | 8/2017 | Sekhavat | |

FOREIGN PATENT DOCUMENTS

| | | |
|---|---|---|
| CA | 2286408 A1 | 3/2001 |
| CN | 103520486 A | 5/2015 |

OTHER PUBLICATIONS

J. Kocsis et al.: Biological Effects of the Metabolites of Dimethyl Sulfoxide. Department of Pharmacology, Thomas Jefferson University (1 Page).
J. Wright: Related Risk. Autism Research News. www.spectrumnews.org. Aug. 11, 2011 (3 Pages).
J. Wright: Immune Disorders during pregnancy boost autism risk in children. Autism Research News. www.spectrumnews.org. Oct. 8, 2015 (4 Pages).
K. Zarbalis: Big brains may hold clue to origins of autism. Autism Research News. www.spectrumnews.org. Feb. 23, 2016 (5 Pages).
C. Nordahl: Early brain enlargement augurs distinct form of autism. Autism Research News. www.spectrumnews.org. Apr. 11, 2017 (3 Pages).
R. Boyle: The brain's secret gardeners. Autism Research News. Feb. 3, 2016 (8 Pages).
A. Griswold: Maternal obesity, genetics may cooperate to up autism risk. www.spectrumnews.org. Nov. 24, 2016 (3 Pages).
N. Zeliadt: Brains of people with autism may be enlarged throughout life. Autism Research News. www.spectrumnews.org. Nov. 13, 2016 (2 Pages).
J. Wright: In autism, brain's emotion hub begins with too many cells. Autism Research News. www.spectrumnews.org. Nov. 13, 2016 (3 Pages).
J. Wright: Brain's immune cells may explain sex bias in autism. Autism Research News. www.spectrumnews.org. May 11, 2017 (3 Pages).
Y. Li et al.: Maternal and Early Postnatal Immune Activation Produce Dissociable Effects on Neurotransmission in mPFC-Amygdala Circuits. The Journal of Neuroscience. Mar. 28, 2018 (15 pages).
L. Weinhard et al.: Microglia remodel synapses by presynaptic trogocytosis and spine head filopodia induction. Nature Communications Article. www.nature.com. 2018 (14pages).
A. Masi et al.: The Immune System, Cytokines, and Biomarkers in Autism Spectrum Disorder. Neurosci. Bull. Apr. 2017 (11 pages).
M. Mahic et al.: Epidemiological and Serological Investigation into the Role of Gestational Maternal Influenza Virus Infection and Autism Spectrum Disorder. Clinical Science and Epidemiology, vol. 2, Issue 3. Jun. 2017 (8 pages).
M. Hornig et al.: Prenatal fever and autism risk. Molecular Psychiatry. www.nature.com. 2017 (8 pages).
K. Moisse: Placenta may hold clues to sex bias in autism. Autism Research News. www.spectrumnews.org. Nov. 16, 2016 (2 Pages).
K. Moisse: Immune molecule may mediate effects of maternal infection. Autism Research News. www.spectrumnews.org. Nov. 16, 2016 (3 Pages).

(Continued)

*Primary Examiner* — Yevgeny Valenrod
(74) *Attorney, Agent, or Firm* — Thrive IP®; Jeremy M. Stipkala

(57) ABSTRACT

Multi-component pharmaceutical compositions perform various functions and confer various benefits by providing methylsulfonylmethane (MSM), fructose diphosphate (FDP), and an herbal component or a nutritional component. Compositions adhering to that pattern have unique and beneficial properties. Such compositions contain only three active components, in order to avoid canceling the positive effects of such compositions when too many components are present. The present claims expand on the work patented in U.S. Pat. Nos. 9,682,048 B1, 10,166,267 B1, and 10,183,053 B1.

15 Claims, No Drawings

(56) References Cited

OTHER PUBLICATIONS

A. Griswold: Microglia-neuron chatter may raise autism risk. www.spectrumnews.org. Nov. 15, 2016 (3 Pages).
N. Zeliadt: Microglia may have only small appetite for synapses. www.spectrumnews.org. Nov. 14, 2016 (3 Pages).
L. Lesko: The impact of inflammation, Risk of Autism linked to mother's immune system dysfunction during pregnancy. Article. (1 Page).
S. Jacob et al.: Dimethyl Sulfoxide (DMSO) in Trauma and Disease (4 pages).
J. Morton et al.: The Effects of Chronic DMSO Administration on the Spontaneous Development of Autoimmune Disease in NZB, BXSB, and MRL/LPR Strain Mice. Department of Medicaine, Pathology, and Surgery. Oregon Health Sciences University (2 Pages).
J. Morton et al.: Effects of Oral Dimethyl Sulfoxide and Dimethyl Sulfone on Murine Autoimmune Lymphoproliferative Disease. Division of Arthritis and Rheumatic Diseases and Department of Pahology. Oregon Health Sciences University 1986 (3 Pages).
L. Milner et al.: Amelioration of Murine Lupus Nephritis by Dimethylsulfoxide. Clinical Immunology and Immunopathology, 45. 1987 (9 pages).
S. Jacob et al.: The Miracle of MSM (5 pages).
M. Butawan et al.: Methylsulfonylmethane: Applications and Safety of a Novel Dietary Supplement. Nutrients 2017. www.mdpi.com (20 pages).
S. Montserrat-De La Paz et al.: Niacin and its metabolites as master regulators of macrophage activation. Science Direct, Journal of Nutritional Biochemistry 39, 2017 (8 Pages).
A. Sauve: NAD+ and Vitamin B3; from Metabolism to Therapies. Perspectives in Pharmacology. The Journal of Pharmacology and Experimental Therapeutics, vol. 324, No. 3. 2007 (11 Pages).
S. Tullius et al.: NAD+ protects against EAE by regulating CD4+ T-Cell differentiation. Nature Communications Article, 2014 (17 Pages).
S. Trammell et al.: Nicotinamide riboside is uniquely and oralyy bioavailable in mice and humans. Nature Communications Article, 2016 (14 Pages).
M. Recio et al.: Anti-Inflammatory Agents from Plants; Progress and Potential. Current Medicinal Chemistry, 2012 (16 Pages).
S. Proudman: Rheumatoid Arthritis and Fish Oil. Dissertation Defense Partial Transcript, Sep. 30, 2013 (3 Pages).
A. Cassidy: Insulin Resistance, Inflammation, Chronic Disease and Anthocyanins. J Nutr. Dec. 11, 2013 (2 Pages).
E. Scott et al.: Less is more for cancer chemoprevention; evidence of a non-linear dose response for the protective effects of resveratrol in humans and mice. HHS Public Access, Sci transl med. Jul. 29, 2015, (27 Pages).
M. Jakobisiak et al.: Natural mechanisms protecting against cancer. Immunology Letters 90 (2003), www.sciencedirect.com, pp. 103-122.
J. Adam et al.: Immune responses in cancer. Pharmacology & Therapeutics 99 (2003), www.sciencedirect.com, pp. 113-132.
M. Anthonavage: Effects or Oral Supplementation With Methylsulfonylmethane on Skin Health and Wrinkle Reduction. Natural medicine Journal, vol. 7, Issue 11. Nov. 2015 (19 Pages).
D. Yao et al.: Effects of Ejiao (colla corii asini) on the hemodynamics, hemorheology and microcirculation during endotoxin shock in dogs. PubMed (Abstract), Jan. 1989, (1 Page).
H. Wu et al.: Hematopoietic Effect of Fractions form the Enzyme-Digested colla corii asini on Mice with 5-Fluorouracil Induced Anemia. The American Journal of Chinese Medicine, vol. 35, No. 5. 2007 (1 Page).
M. Liu et al.: Hematopoietic effects and mechanisms of Fufang E'jiao Jiang on radiotherapy and chemotherapy- induced myelosuppressed mice. Journal of Ethnopharmacology 152, 2014 (9 pages).
D. Wang et al.: Chemical constituents and bioactivities of Colla corii asini. Drug Discoveries and Therapeutics, 2014 (7 pages).

H. Wu et al.: Extraction and identification of collagen-derived peptides with hematopoietic activity from Colla Corii Asini. PubMed (Abstract), Apr. 22, 2016 (2 Pages).
X. Li et al.: Species-specific identification of collagen components in Colla corii asini using a nano-liquid chromatography tamdem mass spectrometry proteomics approach. International Journal of Nanomedicine, 2017 (12 bages).
J. Bardot: Prevent Hair Loss and Stimulate Natural Hair Restoration With Chinese Herbs. www.jbbardot.com. Jan. 15, 2017 (3 Pages).
Hair Care Herbs. www.chagrinvalleysoapandsalve.com (8 Pages).
J. Kang et al.: The effect of CD34+ cell-containing autologous platelet-rich plasma injection on pattern hair loss; a preliminary study. PubMed (Abstract), J Eur Acad Dermatol Venereol, Dec. 2012 (1 Page).
Methylsulfonylmethance (MSM, dimethyl sulfone, crystalline DMSO2, or DMSO2). Alternative Medicine Review, vol. 7, No. 1 2002 (2 pages).
S. Jacob et al.: The Miracle of MSM. The Natural Solution for Pain. (4 pages).
S. Shanmugan al .: The effect of Methylsulfonylmethane on Hair Growth Promotion of Magnesium Ascorbyl Phosphate for the Treatment of Alopecia. Biomolecules & Therapeutics. May 2009 (8 pages).
S. Ahn et al.: Fructose 1, 6-Diphosphate Alleviates UV-Induced Oxidative Skin Damage in Hairless Mice. Pharmaceutical Society of Japan, Biol. Pharm. Bull, vol. 30, No. 4, 2007 (6 Pages).
H. Choi et al.: Fructose 1, 6-diphosphate regulates desmosomal proteins and collagen fibres in human skin equivalents. onlinelibrary.wiley.com. Nov. 2013 (4 Pages).
S. Mohammadi et al.: Protective Effects of Methylsulfonylmethane on Hemodynamics and Oxidative Stress in Monocrotaline-Indued Pulmonary Hypertensive Rats. Advances in Pharmacological Sciences, 2012 (6 Pages).
Boer et al.: Does topical minoxidil increase skin blood flow? A laser doppler flowmetry study. PubMed (Abstract), 1988, (1 Page).
R. Wester et al.: Minoxidil Stimulates Cutaneous Blood Flow in Human Balding Scalps; Pharmacodynamics Measured by Laser Doppler Velocimetry and Photopulse Plethysmography. The Journal of Investigative Dermatology, vol. 82, No. 5. 1984 (3 Pages).
Gillespie: How Urea is made?, Apr. 10, 2018, https://sciencing.com/urea-made-5194345.html, 2015 (3 pages).
Torkos et al. Natural Medicine Journal, 2015, 7(4) 1-5, 2015 (5 pages).
www.centrum.com/whats-inside/products. Jul. 14, 2016 (6 pages).
Life Extension Mix brochure (4 pages).
R. Kurzweil: Weekend Confidential. The Wall Street Journal. May 31, 2014 (2 pages).
Research Article. www.ScienceTranslationalMedicine.org Jul. 29, 2015. vol. 7, issue 298 (1 page).
G. Jensen; The True Value of Antioxidants. www.nutraceuticalsworld.com, Mar. 2013 (2 pages).
www.tandfonline.com, Sep. 19, 2015 (1 page).
J. Whalen: Multivitamins found to have little benefit. The Wall Street Journal. Dec. 17, 2013 (1 page).
R. Jaslow: Multivitamin researchers say case is closed after studies find no health benefits. CBS News. Dec. 16, 2013 (3 pages).
V. Moyer: Vitamin, Mineral, and Multivitamin Supplements for the Primary Prevention of Cardiovascular Disease and Cancer. Annals of Internal Medicine, vol. 160, No. 8. Apr. 15, 2014 (7 pages).
Physicians' Health Study II Releases New Findings on Multivitamin Use, Reduced CVD Risk. Nutritional Outlook. May 2017 (1 page).
S. Rautiainen et al.: Multivitamin Use and the Risk of Cardiovascular Disease in Men. The Journal of Nutrition. Mar. 21, 2016 (6 pages).
S. Rautiainen et al.: Multivitamin use and the risk of hypertension in a prospective Cohort study of women. www.ncbi.nlm.nih.gov. Nov. 6, 2016 (2 pages).
Journal Report: Is It a Good Idea for Adults to Take a Daily Multivitamin? The Wall Street Journal. Apr. 12, 2017 (1 page).
M. Stampfer: Yes People Should Think of Them as Low-Cost Nutritional Insurance Article (1 page).

(56) References Cited

OTHER PUBLICATIONS

E. Guallar: No They Do Little or No Good, and May Be Counterproductive Article (1 page).
J. Kim et al.: Association of Multivitamin and Mineral Supplementation and Risk of Cardiovascular Disease. Circ Cardiovasc Qual Outcomes. Jul. 2018 (14 pages).
Article: Vitamin supplements provide no benefit, study says. The Miami Herald. May 30, 2018. (1 page).
H. Schouweiler et al.: Multivitamins for healthy children: What are the true Benefits? The Journal of Family Practice, vol. 61, No. 8. Aug. 2012 (2 pages).
D. Jenkins et al.: Supplemental Vitamins and Minerals for CVD Prevention and Treatment. Journal of the American College of Cardiology, vol. 71, No. 22. 2018 (15 pages).
M. Cortes-Canteli et al.: Fibinogen and Altered Hemostasis in Alzheimer's Disease. National Institute of Health, J Alzheimers Dis. 2012 (12 pages).
R. Winslow et al.: AARP Magazine Article (1 page).
R. Winslow et al.: Rivals for Warfarin Article. The Wall Street Journal (1 page).
R. Winslow: Medicines Co. Blood Thinner Shows Benefit Article. The Wall Street Journal (1 page).
R. Winslow: Heart Patients May Face a New Drug Dilemma Article. The Wall Street Journal (1 page).
S. Jacob et al.: Dimethyl Sulfoxide (DMSO) in Trauma and Disease. CRC Press (9 pages).
G. Camici et al.: Dimethyl Sulfoxide Inhibits Tissue Factor Expression, Thrombus Formation, and Vascular Smooth Muscle Cell Activation. American Heart Association Inc. 2006 (10 pages).
S. Jacob et al.: The Miracle of MSM. The Natural Solution for Pain. Berkley Books (3 pages).
R. Flaumenhaft: Curbing Clots Article. Harvard Alumni Bulletin, Oct. 2012 (2 pages).
R. Bekendam et al.: Inhibition of Protein Disulfide Isomerase in Thrombosis. Basic & Clinical Pharmacology & Toxicology, 2016 (7 pages).
B. Wright et al.: Insights into dietary flavinoids as molecular templates for the design of anti-platelet drugs. European Society of Cardiology. Cardiovascular Research, Sep. 2012 (10 pages).
Y. Yang et al.: Plant Food Delphinidin-3-Glucoside Significantly Inhibits Platelet Activation and Thrombosis: Novel Protective Roles against Cardiovascular Diseases. www.plosone.org, May 2012, vol. 7, Issue 5 (12 pages).
L. McGinley: New Cancer Treatments Have Perplexing Side Effects. The Washington Post (2 pages).
A. Sorice et al.: Ascorbic Acid; its role in immune system and chronic inflammation diseases. PubMed (Abstract) May 2014 (1 page).
C. Delude: Kept at Bay, In Depth Clinical research, protomag.com, 2015 (5 pages).
Stanford University Medical Center: Bodywide Immune Response Important for Fighting Cancer, Researchers Say. www.dddmag. com, Jan. 20, 2017 (6 pages).
J. Green et al.: Deploying the Body's Army. The Scientist, Apr. 2014 (5 pages).
P. Loftus: Promising Signs for Immunotherapy Drugs Article. The Wall Street Journal, Jun. 3, 2014 (1 page).
S. Nishiumi et al.: Dietary flavonoids as cancer-preventive and therapeutic biofactors. PubMed (Abstract) Jun. 2011 (1 page).
Dimethyl Sulfoxide (DMSO) in Trauma and Disease. Cancer Stem Cells and Differentiation (2 pages).
S. Nguyen: Is Vitamin D a Wonder Pill? Right Now article, Jun. 2015 (2 pages).
Cancer Research UK: Aspirin Could Hold the Key to Supercharged Cancer Immunotherapy. www.dddmag.com, Sep. 4, 2015 (1 page).
M. Marchione: Study; Vitamin B3 May Help Prevent Certain Skin Cancers. www.biosciencetechnology.com, May 14, 2015 (2 pages).
P. Skopinski et al.: In vivo stimulatory effect of multi-component herbal remedy PADMA 28 on mitogen-induced proliferation of mice splenic lymphocytes and their chemokinetic activity. PubMed (Abstract) 2013 (1 page).
S. Costantini et al.: A holistic approach to study the effects of natural antioxidants on inflammation and liver cancer. PubMed (Abstract) 2014 (1 page).
Machine translation of Chinese Patent No. CN-103520486 (2013) (6 pages).
Farris et al. J. Drugs Derm. 12(12), (2013), 1389-1394.
Unpublished U.S. Appl. No. 17/369,947 (78 pages).
Cyprotex US LLC, "Ischemia Challenge in Human Stem Cell Derived Neurons," Report prepared for DEMX, Inc., Oct. 14, 2015 (25 pages).
English language machine translation of Russian Patent RU2478376 (Apr. 10, 204) (11 pages).
Office Action in co-pending U.S. Appl. No. 17/369,947 (Jan. 15, 2025) (6 pages).
University Hospitals "Nutrition Facts" https://uhhospitals. org/heath-information/health-and-wellness-library/article/nutritionfacts-v1/blueberries-raw-1-cup (Year: 2025) (3 pages).

\* cited by examiner

MULTI-COMPONENT NUTRITIONAL SUPPLEMENT FORMULATIONS AND TREATMENT REGIMEN

RELATED APPLICATIONS

This application claims benefit of priority under 35 U.S.C. § 120 and is a continuation of U.S. patent application Ser. No. 17/220,520, filed Apr. 1, 2021, entitled, "MULTI-COMPONENT NUTRITIONAL SUPPLEMENT FORMULATIONS AND TREATMENT REGIMEN," which is a continuation-in-part of U.S. non-provisional application Ser. No. 16/259,304, filed Jan. 28, 2019, entitled, "MULTI-COMPONENT NUTRITIONAL SUPPLEMENT FORMULATIONS AND TREATMENT REGIMEN," which in turn claims benefit of priority under 35 U.S.C. § 119 (e) of U.S. Provisional Application No. 62/709,659, entitled "Nutritional Supplement Treatment Regimen (NSTR™)—Multi-Component Formulations and Methods for the Administration of Nutritional Supplements Including the Multivitamin Delivery System (MDS™), DEMX™, AUTX™, ONCX™, and THROMBX™," filed on Jan. 26, 2018, and U.S. Provisional Application No. 62/761,194, entitled "FLOW AND GLOW™, MULTICOMPONENT FORMULATIONS AND METHODS FOR THE HEALTH AND BEAUTY OF SKIN (INCLUDING LIPS), HAIR AND NAILS," filed on Mar. 15, 2018. Each of the foregoing applications, namely, the '520 non-provisional application, the '304 non-provisional application, the '659 provisional application, and the '194 provisional application, are each incorporated herein by reference in its entirety.

FIELD OF INVENTION

This invention relates to multi-component formulations and methods for the administration and use of nutritional supplements.

BACKGROUND OF THE INVENTION

Nutritional supplements, which include vitamins, herbs, and many other natural substances, are taken by many people in order to remedy nutritional deficiencies, maintain good health, and prevent and treat numerous diseases and disorders. They are the next line of defense after food and lifestyle and before conventional drugs. Unlike most conventional drugs, which are both focused and potent, nutritional supplements are relatively mild and work slowly and in different ways over time. Different nutritional supplements, many of which are plant-based, have different but similar and often overlapping or opposing effects (pathways), including antioxidant, prooxidant, anti-inflammatory, pro-inflammatory, energy metabolism, protein function, blood flow, gene expression, and immune system modulation, among others. The problem is how best to utilize all of the beneficial effects of nutritional supplements.

Contrary to current practice, more is not necessarily better. That is, people now take many different nutritional supplements all at once or randomly in any number and at any time. However, the benefits of nutritional supplements are multiple, similar, overlapping, and sometimes opposing. Each such supplement may be helpful on its own, but together with other supplements which have opposing or even similar effects, such different supplements may cancel each other out ("cancellation effect"). And people are different. A nutritional supplement may benefit different people in different ways and differently at different times. For example, the antioxidant effect of one nutritional supplement may be cancelled out by the prooxidant effect of another nutritional supplement; a nutritional supplement may have an antioxidant effect on one person but a prooxidant effect on another person; a nutritional supplement may be antioxidant at one time and prooxidant at another time. Unlike conventional drugs, whose interactions have been extensively studied but are more immediate, severe, and noticeable, nutritional supplement targets are diverse and multiple and constantly shifting, and the relatively mild effects of nutritional supplements are more likely to cancel each other out. In addition, people generally take many nutritional supplements, which increases the likelihood of the cancellation effect. Nutritional supplement effects are hard to determine to begin with and take a long time to work, and the cancellation effect further diminishes such tenuous benefits. The cancellation effect also hampers bioavailability, which is especially crucial with nutritional supplements' mild effects. And the cancellation effect may interfere with synergy between different nutritional supplements by hampering such interaction. Differing effective plasma levels, common transporters, circadian variations, and other pharmacokinetic and pharmacodynamic factors also contribute to the cancellation effect. Although each nutritional supplement may be beneficial by itself, taking too many nutritional supplements at the same time or randomly will create a hodgepodge of random or even no beneficial effects at all and may eliminate both the additive and synergistic beneficial effects of the nutritional supplements.

The cancellation effect is known. See, for example, U.S. Pat. No. 8,491,889 B1 to Calton et al. The approach of Calton, however, can be improved upon. Exemplary compositions of the '889 patent still include 27, 23, and 28 micronutrients. See, e.g., '889 patent at FIG. 1 and column 7, lines 22-45. Such large numbers of ingredients require a detailed and nearly impossible study of all the possible interactions between the numerous ingredients. A composition of 28 ingredients faces as many as 368 pairs of interactions between ingredients. Considering possible interactions between groups of three or more ingredients, the possible interactions increase by orders of magnitude.

Applicant has found that the cancellation effect is borne out experimentally. In neuron cell testing for viability/survival, where three natural substances increased viability/survival, such benefit was reduced or eliminated by the addition of one or two more such substances to the mix. Testing for neurodegeneration with eight natural substances and transgenic mice showed continued good health and weight gain with no toxicity, but little or no effect on behavior or the histological indicia of cognitive decline.

Another mechanism by which nutritional supplements interact can be called "interference." Short of canceling each other, conflicting nutritional supplements may merely interfere with each other. Each ingredient still confers a benefit, but the benefits are less than if those ingredients were administered independently. Interference can be thought of as the opposite of synergy. Neither nutritional supplement is canceled, but merely diminished. Interference stems from the same root as cancellation. More is not necessarily better due to the inevitable interference resulting from the unprincipled combination of multiple nutritional supplements. Common multivitamin products available on the market today include dozens or even as many as a hundred ingredients. Conflicts due to the cancellation effect and interference between ingredients inhibit the benefit received by the individual consuming the multivitamin product.

SUMMARY OF THE INVENTION

How best to capture the beneficial effects of multiple nutritional supplements? Applicant's Nutritional Supplement Treatment Regimen (NSTR™) is the answer.

The NSTR™ method is the serial and cumulative administration of multiple nutritional supplements in order to minimize, reduce, or eliminate the cancellation effect and interference and give the user the maximum benefit of all such nutritional supplements. In one embodiment, the user first takes a multi-component nutritional supplement composition. Then, at a later time, the user takes a different multi-component nutritional supplement composition, in order to reduce, minimize, or eliminate the cancellation effect of the different multi-component combinations. The end result is that the user receives increased benefit of the nutritional supplements with decreased or minimal cancellation effect or interference. It is impossible to completely eliminate the cancellation effect and interference in all circumstances due to the unlimited potential combinations and the different effects or reactions of different patients.

In certain embodiments of the present invention, a patient may consume one or more of the compositions described herein at different times of the day to reduce or eliminate the cancelation effect and interference between active components. For example, a patient may consume an effective amount of an AUTX™ composition in the morning to reduce inflammation, and an effective amount of a FLOW AND GLOW™ composition in the evening to boost the health of the skin, hair, and nails. Or, a patient may consume one AUTX™ composition in the morning, a different AUTX™ composition at midday, and a third AUTX™ composition in the evening, followed by a THROMBX™ composition at bedtime, for maximum positive effect of the components of the several compositions. These compositions can be consumed or administered in accordance with the NSTR™ method, which provides the user the maximum benefit of all such nutritional supplements while reducing, minimizing, or eliminating the cancellation effect and interference.

Accordingly, certain embodiments of the present invention relate to methods for administering multi-component pharmaceutical compositions to a human patient in need thereof, one such method comprising: administering to the patient a first multi-component pharmaceutical composition consisting essentially of two or more first components at a first time of day; and administering to the patient a different second multi-component pharmaceutical composition consisting essentially of two or more second components at a second time of day. Further embodiments relate to collections of multi-component pharmaceutical compositions. A collection of such compositions indicates compositions that are taken over a given period of time, such as over a day or a few days, but not simultaneously. In some cases, a collection of three multi-component pharmaceutical compositions comprises a first pharmaceutical composition consisting essentially of first components; a second pharmaceutical composition consisting essentially of second components, wherein each of the first components is different than each of the second components; and a third pharmaceutical composition consisting essentially of third components, wherein each of the third components is different than each of the first components and each of the second components. Any suitable number of compositions can be included in a collection, such as, for example, two, three, four, five, six, seven, eight, nine, ten, or more than ten compositions.

Some embodiments of the present invention relate to AUTX™ compositions, such as, for example, multi-component pharmaceutical compositions comprising: a compound chosen from methylsulfonylmethane and dimethyl sulfoxide; vitamin B3; and a natural substance.

Related embodiments provide methods of preventing or treating an autoimmune disease, one such method comprising administering an effective amount of a multi-component pharmaceutical composition comprising:
a compound chosen from methylsulfonylmethane and dimethyl sulfoxide;
vitamin B3; and a natural substance, to a human or animal patient in need thereof.

Further embodiments provide methods of reducing a risk of autism spectrum disorder in a child of a female patient, one such method comprising administering to the female patient an effective amount of a multi-component pharmaceutical composition comprising: a compound chosen from methylsulfonylmethane and dimethyl sulfoxide; vitamin B3; and a natural substance before the female patient becomes pregnant with the child.

Other embodiments of the present invention relate to ONCX™ compositions, such as, for example, multi-component pharmaceutical compositions comprising: three substances chosen from methylsulfonylmethane, dimethyl sulfoxide, selenium, zinc, garlic, *ginseng*, probiotics, astralagus, *echinacea*, olive leaf, ashwagandha, rutin, vitamin A, vitamin B3 vitamin C, vitamin E, folic acid, vitamin B6, vitamin B12, phenols, flavones, phytosterols, curcumin, blueberry, lipoic acid, catechins, flavonoids, and flavonols.

Additional embodiments provide methods of treating or preventing cancer, comprising administering an effective amount of a multi-component pharmaceutical composition comprising: three substances chosen from methylsulfonylmethane, dimethyl sulfoxide, selenium, zinc, garlic, *ginseng*, probiotics, astralagus, *echinacea*, olive leaf, ashwagandha, rutin, vitamin A, vitamin B3 vitamin C, vitamin E, folic acid, vitamin B6, vitamin B12, phenols, flavones, phytosterols, curcumin, blueberry, lipoic acid, catechins, flavonoids, and flavonols, to a human or animal patient in need thereof.

Yet additional embodiments provide THROMBX™ compositions, such as, for example, multi-component pharmaceutical compositions comprising: a compound chosen from methylsulfonylmethane and dimethyl sulfoxide; rutin; and one of docosahexanoic acid (DHA), eicosapentaenoic acid (EPA), and a flavonoid other than rutin.

Yet further embodiments provide methods for treating or preventing thrombosis, one such method comprising administering an effective amount of a multi-component pharmaceutical compositions comprising: a compound chosen from methylsulfonylmethane and dimethyl sulfoxide; rutin; and one of docosahexanoic acid (DHA), eicosapentaenoic acid (EPA), and a flavonoid other than rutin.

The novel two- or three-pronged combination of (a) methylsulfonylmethane, (b) colla corii asini, and (c) optionally resveratrol launches a multifactorial attack on the causes of skin (including lips), hair, and nail deterioration, and at the same time supplements and encourages the factors which contribute to the health and beauty of skin (including lips), hair, and nails, including increased blood flow, antioxidant, and anti-inflammatory effects, and augmented and more pliant collagen. Even more unique, FLOW AND GLOW™ supplies synergy. That is, the increased blood flow generated by colla corii asini, particularly through the smaller capillaries just underlying the skin (including lips), hair, and nails, as augmented by MSM, both as a blood diluent and possibly an antithrombotic blood flow enhancer, will transport the many benefits of all three components directly to the skin (including lips), hair, and nails, for all the world to see.

Accordingly, certain additional embodiments relate to FLOW AND GLOW™ compositions, such as, for example, multi-component pharmaceutical compositions comprising: methylsulfonylmethane; colla corii asini; and optionally resveratrol.

Further embodiments relate to methods of improving the beauty, appearance, and/or health of skin, including lips, hair, nails, or a combination thereof, comprising administering an effective amount of a multi-component pharmaceutical composition comprising methylsulfonylmethane; colla corii asini; and optionally resveratrol, to a human or animal patient in need thereof.

While the disclosure provides certain specific embodiments, the invention is not limited to those embodiments. A person of ordinary skill will appreciate from the description herein that modifications can be made to the described embodiments and therefore that the specification is broader in scope than the described embodiments. All examples are therefore non-limiting.

DETAILED DESCRIPTION

As required, detailed embodiments of the present invention are disclosed herein; however, it is to be understood that the disclosed embodiments are merely exemplary of the invention that may be embodied in various forms. Therefore, specific structural and functional details disclosed herein are not to be interpreted as limiting, but merely as a basis for the claims and as a representative basis for teaching one skilled in the art to variously employ the present invention.

Unless defined otherwise, all technical and scientific terms used herein have the same meaning as is commonly understood by one of ordinary skill in the art to which this disclosure belongs. In the event that there is a plurality of definitions for a term herein, those in this section prevail unless stated otherwise.

Wherever the phrase "for example," "such as," "including" and the like are used herein, the phrase "and without limitation" is understood to follow unless explicitly stated otherwise. Similarly, "an example," "exemplary" and the like are understood to be non-limiting.

The term "substantially" allows for deviations from the descriptor that do not negatively impact the intended purpose. Descriptive terms are understood to be modified by the term "substantially" even if the word "substantially" is not explicitly recited.

The term "about" when used in connection with a numerical value refers to the actual given value, and to the approximation to such given value that would reasonably be inferred by one of ordinary skill in the art, including approximations due to the experimental and or measurement conditions for such given value.

The terms "comprising" and "including" and "having" and "involving" (and similarly "comprises", "includes," "has," and "involves") and the like are used interchangeably and have the same meaning. Specifically, each of the terms is defined consistent with the common United States patent law definition of "comprising" and is therefore interpreted to be an open term meaning "at least the following," and is also interpreted not to exclude additional features, limitations, aspects, etc. Thus, for example, "a device having components a, b, and c" means that the device includes at least components a, b and c. Similarly, the phrase: "a method involving steps a, b, and c" means that the method includes at least steps a, b, and c.

Unless the context clearly requires otherwise, throughout the description and the claims, the words "comprise", "comprising", and the like are to be construed in an inclusive sense as opposed to an exclusive or exhaustive sense; that is to say, in the sense of "including, but not limited to".

Any discussion of the prior art throughout the specification should in no way be considered as an admission that such prior art is widely known or forms part of common general knowledge in the field.

It is an object of the present invention to overcome or ameliorate at least one of the disadvantages of the prior art, or to provide a useful alternative.

As used herein, the term "administering" refers to providing a therapeutically effective amount of a formulation or pharmaceutical composition to a patient, using intravitreal, intraocular, ocular, subretinal, intrathecal, intravenous, subcutaneous, transcutaneous, intracutaneous, intracranial, topical and the like administration. The formulation or pharmaceutical compound of the present invention can be administered alone, but may be administered with other compounds, excipients, fillers, binders, carriers or other vehicles selected based upon the chosen route of administration and standard pharmaceutical practice. Administration may be by way of carriers or vehicles, such as injectable solutions, including sterile aqueous or non-aqueous solutions, or saline solutions; creams; lotions; capsules; tablets; granules; pellets; powders; suspensions, emulsions, or microemulsions; patches; micelles; liposomes; vesicles; implants, including microimplants; eye drops; other proteins and peptides; synthetic polymers; microspheres; nanoparticles; and the like.

The formulations or pharmaceutical composition of the present invention may also be included, or packaged, with other non-toxic compounds, such as pharmaceutically acceptable carriers, excipients, binders and fillers including, but not limited to, glucose, lactose, gum acacia, gelatin, mannitol, xanthan gum, locust bean gum, galactose, oligosaccharides and/or polysaccharides, starch paste, magnesium trisilicate, talc, corn starch, starch fragments, keratin, colloidal silica, potato starch, urea, dextrans, dextrins, and the like. Specifically, the pharmaceutically acceptable carriers, excipients, binders, and fillers contemplated for use in the practice of the present invention are those which render the compounds of the invention amenable to intravitreal delivery, intraocular delivery, ocular delivery, subretinal delivery, intrathecal delivery, intravenous delivery, subcutaneous delivery, transcutaneous delivery, intracutaneous delivery, intracranial delivery, topical delivery and the like. Moreover, the packaging material may be biologically inert or lack bioactivity, such as plastic polymers, silicone, etc., and may be processed internally by the patient without affecting the effectiveness of the composition/formulation packaged and/or delivered therewith.

The phrase "effective amount" as applied to the formulations and compositions and collections described herein, means the amount necessary to render the desired therapeutic result. For example, an effective amount is a level effective to treat, cure, or alleviate the symptoms of a disorder for which the therapeutic compound, biologic or composition is being administered. Amounts effective for the particular therapeutic goal sought will depend upon a variety of factors including the disorder being treated and its severity and/or stage of development/progression; the bioavailability, and activity of the specific compound or formulation used; the route or method of administration and introduction site on the patient; the rate of clearance of the specific compound or biologic and other pharmacokinetic properties; the duration of treatment; inoculation regimen; drugs used in combination or coincident with the specific composition or formulation; the age, body weight, sex, diet, physiology and general health of the patient being treated; and like factors well known to one of skill in the relevant scientific art. Some variation in dosage will necessarily occur depending upon the condition of the patient being treated, and the physician or other individual administering treatment will, in any event, determine the appropriate dose for an individual patient.

As used herein, "disorder" refers to a disorder, disease or condition, or other departure from healthy or normal biological activity, and the terms can be used interchangeably. The terms refer to any condition that impairs normal function. The condition may be caused by sporadic or heritable genetic abnormalities. The condition may also be caused by non-genetic abnormalities. The condition may also be caused by injuries to a patient from environmental factors, such as, but not limited to, cutting, crushing, burning, piercing, stretching, shearing, injecting, or otherwise modifying a patient's cell(s), tissue(s), organ(s), system(s), or the like.

As used herein, "treatment" or "treating" refers to arresting or inhibiting, or attempting to arrest or inhibit, the progression of a disorder and/or causing, or attempting to cause, the reduction, suppression, regression, or remission of a disorder and/or a symptom thereof. As would be understood by those skilled in the art, various clinical and scientific methodologies and assays may be used to assess the development or progression of a disorder, and similarly, various clinical and scientific methodologies and assays may be used to assess the reduction, regression, or remission of a disorder or its symptoms.

As used herein, "prevention" or "preventing" refers to arresting or inhibiting, or attempting to arrest or inhibit, the initial onset or development of a disorder. The prevention of a disorder may occur before any clinical signs of the disorder being prevented are recognized.

The ingredients used herein can appear in any suitable form. Pharmaceutically acceptable stereoisomers, tautomers, topoisomers, vitamers, prodrugs, and metabolites, and the pharmaceutically acceptable salts, hydrates, solvates, and chelates of any of the foregoing can be employed, alone or in combination. Examples of the varieties of forms of those ingredients appear in this specification.

Any suitable dose can be used in a single administration of a composition of the present invention. A possible dose of the active ingredients varies within a wide range and will depend on various factors such as the relevant indication, the route of administration, the age, weight and sex of the patient, and may be determined by a physician. Pharmacokinetic, pharmacodynamic, and other considerations may alter the dose actually administered to a higher or lower value. In general, total daily dose administration to a patient in single or individual doses, may be in amounts, for example, from 0.001 to 10 mg/kg body weight daily, and more usually from 0.01 to 1,000 mg per day, of total active ingredients. Such dosages will be administered to a patient in need of treatment from one to three times each day, or as often as needed for efficacy, and for periods of at least two months, more typically for at least six months, or chronically. Accordingly, the compositions of the present invention can appear in any suitable dosage form. For example, such compositions can be in the form of a tablet, pill, lozenge, dragee, troche, hard or soft capsule, powder, cachet, granule, suppository, solution, aqueous or oily suspension, emulsion, lotion, syrup, ointment, gel, paste, cream, foam, vapor, spray, aerosol, or transdermal patch.

Following are several examples (embodiments) of the NSTR™ method. As explained herein, the Nutritional Supplement Treatment Regimen (NSTR™), relates to methods for the administration and use of nutritional supplements and multi-component formulations such as pharmaceutical compositions containing those components.

MDS™

The Multivitamin Delivery System (MDS™) provides one example of the NSTR™ method. Despite universal and longstanding acceptance and use, multivitamins (which are an olla podrida of nutritional supplements) have proven largely ineffective in large studies. The theory behind multivitamins is sound, namely to satisfy multiple nutritional needs. The problem is that many of the intended benefits of the multivitamins do not reach the user. Why? Commercially available multivitamins include up to 30 or more components. The odds of the cancellation effect and interference approach 100%. The solution? The MDS™ method. A 30 component multivitamin, for example, is divided into separate and smaller formulations of fewer components. For example, 3 formulations of 10 components, 5 formulations of 6 components, 6 formulations of 5 components, or even 10 formulations of 3 components, in order to reduce, minimize, or eliminate the cancellation effect and interference between such formulations. Such formulations, together called "a collection," are then taken at regular intervals during the day. Any number of components can be divided this way, even a list of 100 or more components. The end result is that the user receives the maximum benefit of the multivitamin with decreased or minimal cancellation effect or interference, and the multivitamin actually lives up to its name. Such methods of use/administration will maximize the preventive effects over time of all embodiments of the NSTR™ method.

Certain embodiments of the present invention relate to treating or preventing age-related degeneration. Aging is a risk factor for practically everything. In general, degeneration increases with age, and a major purpose of nutritional supplements is to prevent, delay, and minimize degeneration. Therefore, as an additional method of use for all embodiments of the NSTR™ method, the individual or multi-component formulations will be administered to all people of a certain age, regardless of symptoms or any demonstrated need. For example, DEMX™ composition administration could begin uniformly at age 50, since the prodromal time period for developing Alzheimer's Disease ("AD") is estimated to be 15 to 20 years. Alternatively, administration could begin at the first signs of degeneration (neurodegeneration for DEMX™ compositions), as determined by relevant biomarkers (bloodwork, imaging, and cerebrospinal fluid levels for DEMX™ compositions), regardless of chronological age.

Unexpectedly, it has been found that a three-component multi-component pharmaceutical composition strikes the right balance between supplying beneficial components, possibly enjoying synergies between such components, and avoiding cancellation effects and interference, in some embodiments. The greater number of components dramatically increases the chance for cancellation effects and interference between two or more components. As described above, certain embodiments of the present invention relate to methods for administering multi-component pharmaceutical compositions to a human patient in need thereof, one such method comprising: administering to the patient a first multi-component pharmaceutical composition consisting essential of three or more first components at a first time of day; and administering to the patient a second multi-component pharmaceutical composition consisting essentially of three or more second components at a second time of day, wherein at least one of the three or more first components is different than at least one of the three or more second components.

Further embodiments provide for three compositions of ten components each. In some cases, one of the three compositions comprises methylsulfonylmethane. In other cases, the three compositions comprise (a) methylsulfonylmethane; (b) one or more of vitamin B3 and rutin; and (c) one or more of selenium, zinc, garlic, *ginseng*, probiotics, astralagus, *echinacea*, olive leaf, ashwagandha, rutin, vitamin A, vitamin C, vitamin E, folic acid, vitamin B6, vitamin B12, phenols, flavones, phytosterols, curcumin, blueberry, lipoic acid, resveratrol, green tea, vitamin D, docosahexanoic acid (DHA), eicosapentaenoic acid (EPA), pomegranate, quercetin, cocoa, catechins, anthocyanins, purple grape products, red wine extract, cranberry, flavonoids, and flavonols, spread across three compositions. In other cases, three compositions can be similarly constructed so that each composition comprises, for example, three, five, ten, fifteen, or twenty components, or a combination thereof. For example, one composition could include three components, and another composition contains fifteen components, and a third composition includes nine components.

A cancellation effect or interference between components can arise from any suitable mechanism, whether it be chemical reaction between the two components in the pill or capsule or other administration form, chemical reaction between the two components upon administration, competition for absorption into the body, or competition for particular binding sites or active sites within the body after absorption, among other possible mechanisms.

The form of the multi-component pharmaceutical compositions can be any suitable dosage form. In some cases, the first multi-component pharmaceutical composition is present in a first form, and the second multi-component pharmaceutical composition is present in a second form, and the first form differs from the second form by phase, shape, color, size, name, number of dosage forms, packaging, or a combination thereof. For example, the first multi-component pharmaceutical composition can be present in a first form such as a tablet, pill, lozenge, dragee, troche, hard or soft capsule, powder, cachet, granule, suppository, solution, aqueous or oily suspension, emulsion, lotion, syrup, ointment, gel, paste, cream, foam, vapor, spray, aerosol, or transdermal patch. Similarly, the second multi-component pharmaceutical composition can be present in a second form such as a tablet, pill, lozenge, dragee, troche, hard or soft capsule, powder, cachet, granule, suppository, solution, aqueous or oily suspension, emulsion, lotion, syrup, ointment, gel, paste, cream, foam, vapor, spray, aerosol, or transdermal patch. To aid the caregiver or the patient in distinguishing between the two compositions, the two forms may be different in some easily-cognizable aspect.

The first multi-component pharmaceutical composition and the second multi-component pharmaceutical composition (and any further multi-component pharmaceutical compositions) can be any suitable composition. For example, DEMX™, AUTX™, ONCX™, THROMBX™, "FLOW AND GLOW™ compositions described herein can be used alone or in combination in accordance with this aspect of the invention. For example, a first DEMX™ composition can be administered in the morning, while a second, different DEMX™ composition can be administered in the evening. Or, an ONCX™ composition can be administered at breakfast, and a FLOW AND GLOW™ composition can be administered at dinner.

The first, second, and third multi-component pharmaceutical compositions need not be completely different. Only one of the three or more components of one need differ from one of the three or more components of the other. The differing ingredients are not compatible, in certain instances of the present invention. In other circumstances, all three compositions are different, and have no component in common with any two of those compositions.

Two and three multi-component pharmaceutical compositions have been described here, but the number of such compositions, and the number of components in such compositions, are not limited. For example, a first multi-component pharmaceutical composition can be administered in the morning; a second multi-component pharmaceutical composition can be administered at mid-day; a third multi-component pharmaceutical composition can be administered in the evening, and a fourth multi-component pharmaceutical composition can be administered at bedtime. For another example, various multi-component pharmaceutical compositions can be administered throughout the day or even around the clock. In some instances, any cancellation effect or interference can be minimized or eliminated if at least an hour passes between administration of one multi-component pharmaceutical composition and another. Some embodiments of the present invention comprise three compositions consisting essentially of numerous components each, wherein none of the three compositions includes a component also present in another of the three compositions. Three compositions each consisting essentially of 20, 20, and 20 different components, with no component appearing in two of those compositions, appear in certain instances of the present invention. Three compositions each consisting essentially of five, five, and five different components, with no component appearing in two of those compositions, appear in other instances of the present invention.

In some cases, a multi-component pharmaceutical composition comprises no more than ten active components. Inert carriers, excipients, diluents, and the like are not counted among the active components, and can increase the number of ingredients beyond ten, for example. Such a composition consists essentially of the ten active components. In other cases, a multicomponent pharmaceutical composition consists essentially of no more than nine, no more than eight, no more than seven, no more than six, no more than five, no more than four, or no more than three active components. Such compositions elegantly advance over known compositions with Applicant's unexpected "less is more" discovery. Complex cancellation effects and the need for excruciating comparisons of all ingredients in an overloaded composition are avoided by simply reducing the potential for such effects.

DEMX™

In some embodiments, a DEMX™ composition is a three-component nutritional supplement formulation useful as a method for the prevention or delay of neurodegeneration and cognitive decline, including AD. Two of the components of each formulation are methylsulfonylmethane (MSM) and fructose diphosphate (FDP). There are numerous third components which are also nutritional supplements, including but not limited to resveratrol (patent granted), docosahexaenoic acid (DHA) (patent granted), blueberry (patent granted), curcumin (patent granted), trehalose (patent granted), ashwagandha (patent granted), rutin (patent granted), and green tea (patent granted). U.S. Pat. Nos. 9,682,048 B1, 10,166,267 B1, and 10,183,053 B1 are each incorporated herein by reference in its entirety. The purpose of DEMX™ compositions is to counter the multiple contributing causes and factors of neurodegeneration and AD by enlisting and encouraging the body's own defense mechanisms. Neuron cell testing of DEMX™ compositions has demonstrated both the cancellation effect and the efficacy of some of the formulations. The treatment regimen for DEMX™ compositions is to take the same or a different three-component formulation at regular intervals during the day. The end result of DEMX™ composition administration is that the user receives the maximum benefit of all of the third components, with decreased or minimal cancellation effect and interference, along with the benefits of the MSM/FDP combination.

AUTX™

In some embodiments, an AUTX™ composition is a three-component nutritional supplement formulation useful as methods for the prevention and treatment of autoimmune diseases, including autism spectrum disorder (ASD). Autoimmune diseases and disorders, including lupus, rheumatoid arthritis, inflammatory bowel disease, polymyalgia, fibromyalgia, chronic fatigue syndrome, type 1 diabetes, and other chronic inflammatory disorders, are among the most intractable. They are caused by an immune system out of control and which attacks rather than defends the body, primarily through excessive and untimely inflammation. Such diseases are widespread, particularly among women, and because of mis- or under-diagnosis, probably more widespread than they appear. They are usually not life threatening, but they involve continual daily suffering, with ups and downs from day to day, good days and bad days, a struggle to exist. Conventional drugs are only briefly palliative, do not correct the causes, and have significant side effects, which preclude their long-term use.

Some embodiments of the AUTX™ compositions provide three-component formulations such as (1) MSM and vitamin B3 and any other such natural substance except DMSO (2) DMSO and vitamin B3 and any other such natural substance except MSM and (3) any three such natural substances other than DMSO, MSM, and vitamin B3. The treatment regimen for AUTX™ is to take the same or a different pharmaceutical composition such as a three-component formulation at regular intervals during the day. The end result of AUTX™ is to maximize the anti-inflammatory effects of such natural substances, in order to modulate to the maximum extent possible the user's dysfunctional immune system, with decreased or minimal cancellation effect or interference. The autoimmune patient will also know that there is hope and the possibility of some relief, which will reduce the stress which is one likely cause of the disease itself and also an aggravating factor in the daily suffering.

AUTX™ compositions and the NSTRT method may also be used for treating or preventing autism spectrum disorder (ASD). One theory of ASD is that it results in part from an autoimmune disorder (defined to include obesity) in the mother, which disorder results in incomplete and ineffective synaptic pruning in the fetus. Synaptic pruning is in part a prenatal process which eliminates unnecessary neurons from the developing brain. Inadequate synaptic pruning may result in excessive and undifferentiated neuronal growth resulting in ASD. Synaptic pruning is an immune system related function which is regulated by microglia, death receptor 6, the complement protein cascade, and other immune system proteins, including major histocompatibility complex class 1. One possible cause of defective synaptic pruning is the reaction of the fetus's brain to maternal inflammation and antibrain antibodies resulting from the mother's autoimmmune disorder. Differing degrees of inadequate synaptic pruning may cause differing degrees/phenotypes of autistic symptoms, accounting for the spectrum. This theory may also explain the predominance of ASD in boys (80%) in that the female fetus's immune system, as a result of similarity or some other factor relating to the mother's immune system, may have more resistance to the mother's inflammation and antibrain antibodies. The use of AUTX™ compositions for ASD prevention must precede pregnancy, since intervention during pregnancy is too risky and likely too late.

Accordingly, some embodiments of the present invention relate to multi-component pharmaceutical compositions comprising: a compound chosen from methylsulfonylmethane and dimethyl sulfoxide; vitamin B3; and a natural substance. In some cases, the compound is methylsulfonylmethane. In other cases, the compound is dimethyl sulfoxide. Any suitable amount of compound can be present. For example, in certain instances, the compound is present in an amount ranging from about 0.01% to about 90% by weight. In other instances, the compound is present in an amount of at least about 0.01%, at least about 0.1%, at least about 0.5%, at least about 1%, at least about 2%, at least about 3%, at least about 4%, at least about 5%, at least about 10%, at least about 20%, or at least about 50% by weight. Still further instances provide that the compound is present in an amount of no more than about 0.1%, no more than about 0.5%, no more than about 1%, no more than about 2%, no more than about 3%, no more than about 4%, no more than about 5%, no more than about 10%, no more than about 20%, no more than about 50%, or no more than about 90% by weight.

Vitamin B3 can be present in any suitable form, and in any suitable amount. Further instances of the present invention provide the vitamin B3 as niacin, niacinamide, or niacinamide riboside. Additional instances allow the vitamin B3 to be present in an amount ranging from about 0.01% to about 90% by weight. Other instances allow the vitamin B3 to be present in an amount of at least about 1%, at least about 2%, at least about 3%, at least about 4%, at least about 5%, at least about 10%, at least about 20%, or at least about 50% by weight. In still further instances, the vitamin B3 is present in an amount of no more than about 1%, no more than about 2%, no more than about 3%, no more than about 4%, no more than about 5%, no more than about 10%, no more than about 20%, no more than about 50%, or no more than about 90% by weight.

Any suitable natural substances can be used in the AUTX™ compositions. For example, in some cases, the natural substance is chosen from ashwagandha, curcumin, resveratrol, green tea, rutin, vitamin D, docosahexanoic acid (DHA), eicosapentaenoic acid (EPA), pomegranate, quercetin, cocoa, and combinations of two or more thereof. In other cases, the natural substance is one of ashwagandha, curcumin, resveratrol, green tea, rutin, vitamin D, docosahexanoic acid (DHA), eicosapentaenoic acid (EPA), pomegranate, quercetin, and cocoa. In still other cases, the natural substance can be blueberry.

For completeness, in some cases, AUTX™ compositions comprise methylsulfonylmethane (MSM), fructose 1,6-diphosphate (FDP), and one or more natural substances chosen from docosahexanoic acid (DHA), resveratrol, and blueberry, and combinations thereof. In further cases, AUTX™ compositions comprise methylsulfonylmethane (MSM), fructose 1,6-diphosphate (FDP), and at least one of an herbal component or a nutritional component comprising curcumin. U.S. Pat. Nos. 9,682,048 B1 and 10,166,267 B1 are incorporated herein by reference in their entirety. Applicant has discovered, unexpectedly, that useful compositions may comprise more than about 5% by weight of methylsulfonylmethane. Accordingly, some embodiments comprise methylsulfonylmethane (MSM), fructose 1,6-diphosphate (FDP), and one or more natural substances chosen from docosahexanoic acid (DHA), resveratrol, and blueberry, and combinations thereof, wherein the methylsulfonylmethane (MSM) is present in an amount of greater than about 5% by weight, at least about 10% by weight, at least about 20% by weight, at least about 30% by weight, at least about 40% by weight, at least about 50% by weight, at least about 60% by weight, at least about 70% by weight, at least about 80% by weight, or at least about 90% by weight MSM. Other embodiments comprise methylsulfonylmethane (MSM), fructose 1,6-diphosphate (FDP), and one or more natural substances chosen from docosahexanoic acid (DHA), resveratrol, and blueberry, and combinations thereof, wherein the methylsulfonylmethane (MSM) is present in an amount of no more than about 10% by weight, no more than about 20% by weight, no more than about 30% by weight, no more than about 40% by weight, no more than about 50% by weight, no more than about 60% by weight, no more than about 70% by weight, no more than about 80% by weight, or no more than about 90% by weight MSM. Further embodiments comprise methylsulfonylmethane (MSM), fructose 1,6-diphosphate (FDP), and at least one of an herbal component or a nutritional component comprising curcumin, wherein the methylsulfonylmethane (MSM) is present in an amount of greater than about 5% by weight, at least about 10% by weight, at least about 20% by weight, at least about 30% by weight, at least about 40% by weight, at least about 50% by weight, at least about 60% by weight, at least about 70% by weight, at least about 80% by weight, or at least about 90% by weight MSM. Still other embodiments comprise methylsulfonylmethane (MSM), fructose 1,6-diphosphate (FDP), and at least one of an herbal component or a nutritional component comprising curcumin, wherein the methylsulfonylmethane (MSM) is present in an amount of no more than about 10% by weight, no more than about 20% by weight, no more than about 30% by weight, no more than about 40% by weight, no more than about 50% by weight, no more than about 60% by weight, no more than about 70% by weight, no more than about 80% by weight, or no more than about 90% by weight MSM.

As used herein, nutritional supplements and natural substances include herbal components and nutritional components. Herbal components can be said to include, but are not limited to, plant leaves, stems, seeds, flowers, and/or roots and their extracts such as alfalfa, barley grass, blessed thistle, cauliflower, *chlorella*, cilantro, dandelion, flax seed, Japanese knotweed, kelp, lemon balm, lemon grass, nettle, plantain, sunflower seed, Siberian eleuthero, wheat grass, *spirulina* and other blue green algae extract, and mixtures thereof. Nutritional components can be said to include, but are not limited to, fruits, vegetables, and their extracts such as açaí, apple, asparagus, banana, beet, blueberry, broccoli, brussels sprout, cabbage, carrot, cranberry, cucumber, grape, grapefruit, hawthorn berry, lemon, lime, orange, pea, pear, pineapple, plum, pomegranate, pumpkin, raspberry, spinach, strawberry, tangerine, tart cherry, and tomato, enzymes such as alpha galactosidase, amylase, bromelain, cellulase, coenzyme Q10, invertase, lactase, lipase, papain, peptidases including protease I and protease II, mushrooms and their extracts such as agarikon (laricifomes *officinalis* and/or fomitopsis *officinalis*), chaga (inonotus obliquus), enokitake (flammulina velutipes), himematsutake (*agaricus brasiliensis, agaricus* blazei), kawaratake (*trametes versicolor*), maitake (grifola *frondosa*), mesima (*phellinus* linteus), oyster hirotaka (*pleurotus* ostreatus), reishi (*Ganoderma lucidum*), shiitake (*lentinula edodes*), yamabushitake (hericium *erinaceus*), and Zhu Ling (grifola *umbellata*), and other substances such as betaine HCl, choline, eriocitrin, fructose diphosphate (FDP), hesperidin, inositol, naringin, narirutin, resveratrol, rutin, and lutein, so-called minerals and their salts and chelates such as calcium, copper, iodine, iron, magnesium, manganese, molybdenum, potassium, selenium, sodium, and zinc, vitamins in one or more of their known forms such as vitamin A (as beta carotene and/or retinyl acetate, for example), vitamin B3 (niacin, nicotinamide, and/or nicotinamide riboside), vitamin B6, vitamin B12, vitamin C, vitamin D3, vitamin E, vitamin K1, riboflavin, biotin, folic acid, pantothenic acid, and thiamine, and mixtures of two or more of any of the foregoing.

Any suitable amount of the natural substance can be present. Sometimes, the natural substance is present in an amount ranging from about 0.01% to about 90% by weight of the composition. Other times, the natural substance is present in an amount of at least about 1%, at least about 2%, at least about 3%, at least about 4%, at least about 5%, at least about 10%, at least about 20%, or at least about 50% by weight. Still other times, the natural substance is present in an amount of no more than about 1%, no more than about 2%, no more than about 3%, no more than about 4%, no more than about 5%, no more than about 10%, no more than about 20%, no more than about 50%, or no more than about 90% by weight.

Related embodiments provide methods of preventing or treating an autoimmune disease, one such method comprising administering an effective amount of a multi-component pharmaceutical composition comprising:

a compound chosen from methylsulfonylmethane and dimethyl sulfoxide; vitamin B3; and a natural substance, to a human or animal patient in need thereof.

Further embodiments provide methods of reducing a risk of autism spectrum disorder in a child of a female patient, one such method comprising administering to the female patient an effective amount of a multi-component pharmaceutical composition comprising: a compound chosen from methylsulfonylmethane and dimethyl sulfoxide; vitamin B3; and a natural substance before the female patient becomes pregnant with the child. As used herein, an "autism spectrum disorder" includes obesity.

ONCX™

In certain embodiments, an ONCX™ composition is a three-component nutritional supplement formulation useful in methods for the prevention and treatment of cancer. Immunotherapy, defined to include the body's own immune system and other endogenous protective systems, is the most desirable alternative for cancer prevention and treatment. The idea is to stimulate and strengthen such systems, which are interrelated and work together, in order to assist the body itself in preventing the cancer from forming (including as the result of random mutations) and then, if the cancer does form, halting or weakening its survival and spread. These systems already nip most potential cancers in the bud, and augmented protective systems will do an even better job. Targeted immune system modification is another alternative. There is also research suggesting that cancer formation requires an epigenetic reprogramming to stem cell status from which the cancer starts to grow, and that such reprogramming requires an as yet undiscovered trigger, perhaps inflammation.

There are many different drugs currently used in immunotherapy. However, many of them have serious side effects, which limit their usefulness and particularly their long-term use. Also, because of human heterogeneity, such drugs are ineffective for many people. On the other hand, there are many natural substances which are reported to bolster the body's immune and other endogenous protective systems, but which do so more slowly and mildly than drugs and over a longer period of time.

Suitable natural substances include, for example, methylsulfonylmethane, dimethyl sulfoxide, selenium, zinc, garlic, *ginseng*, probiotics, astralagus, *echinacea*, olive leaf, ashwagandha, rutin, vitamin A, vitamin B3 vitamin C, vitamin E, folic acid, vitamin B6, vitamin B12, phenols, flavones, phytosterols, curcumin, blueberry, lipoic acid, resveratrol, green tea, vitamin D, docosahexanoic acid (DHA), eicosapentaenoic acid (EPA), pomegranate, quercetin, cocoa, catechins, flavonoids, and flavonols.

The mechanisms of action of these natural substances are varied but poorly understood. They include antioxidant and anti-inflammatory effects on the immune system itself, along with protection against DNA damage caused by reactive oxygen species (ROS) and chronic inflammation. Some substances directly enhance the body's own endogenous antioxidant and anti-inflammatory defenses. Some substances support the body's own proteostasis repair network and protein quality control, which helps maintain normal noncancerous homeostasis. In the aggregate these natural substances marshal all of the body's internal defense systems in order to attack and eliminate the cancer at the earliest possible stage. And even if such defense mechanisms fail to stop the cancer from forming, they will assist the body's effort to minimize and restrict its survival and spread.

The ONCX™ composition treatment regimen is first to reduce the natural substances to three-component formulations, in order to reduce, minimize, or eliminate the cancellation effect and interference. The user then takes one such formulation and then the same or different formulations at regular intervals during the day. The desired end result of ONCX™ composition administration is that the user receives the maximum benefit of such nutritional supplement formulations with decreased or minimal cancellation effect or interference.

Other embodiments of the present invention relate to multi-component pharmaceutical compositions comprising: a compound chosen from three substances chosen from methylsulfonylmethane, dimethyl sulfoxide, selenium, zinc, garlic, *ginseng*, probiotics, astralagus, *echinacea*, olive leaf, ashwagandha, rutin, vitamin A, vitamin B3 vitamin C, vitamin E, folic acid, vitamin B6, vitamin B12, phenols, flavones, phytosterols, curcumin, blueberry, lipoic acid, resveratrol, green tea, vitamin D, docosahexanoic acid (DHA), eicosapentaenoic acid (EPA), pomegranate, quercetin, cocoa, catechins, flavonoids, and flavonols. Still further embodiments relate to multi-component pharmaceutical compositions comprising: three substances chosen from selenium, zinc, garlic, *ginseng*, probiotics, astralagus, *echinacea*, olive leaf, ashwagandha, rutin, vitamin A, vitamin B3 vitamin C, vitamin E, folic acid, vitamin B6, vitamin B12, phenols, flavones, phytosterols, curcumin, blueberry, lipoic acid, resveratrol, green tea, vitamin D, docosahexanoic acid (DHA), eicosapentaenoic acid (EPA), pomegranate, quercetin, cocoa, catechins, flavonoids, and flavonols.

In certain cases, however, some compounds can be excluded. For example, sometimes the ONCX™ composition does not include vitamin B3. Other times, the composition does not include rutin.

The components can be present in any suitable amount. For example, in certain instances, the one of the three components is present in an amount ranging from about 0.01% to about 90% by weight. In other instances, one of the three components is present in an amount of at least about 0.01%, at least about 0.1%, at least about 0.5%, at least about 1%, at least about 2%, at least about 3%, at least about 4%, at least about 5%, at least about 10%, at least about 20%, or at least about 50% by weight. Still further instances provide that one of the three components is present in an amount of no more than about 0.1%, no more than about 0.5%, no more than about 1%, no more than about 2%, no more than about 3%, no more than about 4%, no more than about 5%, no more than about 10%, no more than about 20%, no more than about 50%, or no more than about 90% by weight.

The three substances that can be used in an ONCX™ composition are not limited. In some cases, the three substances are chosen from methylsulfonylmethane, dimethyl sulfoxide, selenium, zinc, garlic, *ginseng*, astralagus, *echinacea*, olive leaf, ashwagandha, rutin, vitamin A, vitamin B3 vitamin C, vitamin E, folic acid, vitamin B6, vitamin B12, curcumin, blueberry, lipoic acid, anthocyanins, purple grape products, red wine extract, and cranberry. Furthermore, any suitable amount of the three substances can appear. For example, the three substances can be present in an ONCX™ composition in an amount ranging from about 0.02% to about 90% by weight. For another example, the three substances are present in an amount of at least about 1%, at least about 2%, at least about 3%, at least about 4%, at least about 5%, at least about 10%, at least about 20%, or at least about 50% by weight. An additional example provides that the three substances are present in an amount of no more than about 1%, no more than about 2%, no more than about 3%, no more than about 4%, no more than about 5%, no more than about 10%, no more than about 20%, no more than about 50%, or no more than about 90% by weight.

Any suitable flavonoids can be used in an ONCX™ composition. In some cases, the flavonoids are chosen from anthocyanins, purple grape products, red wine extract, and cranberry.

Additional embodiments provide methods of treating or preventing cancer, comprising administering an effective amount of a multi-component pharmaceutical composition comprising: a compound chosen from three substances chosen from methylsulfonylmethane, dimethyl sulfoxide, selenium, zinc, garlic, *ginseng*, probiotics, astralagus, *echinacea*, olive leaf, ashwagandha, rutin, vitamin A, vitamin B3 vitamin C, vitamin E, folic acid, vitamin B6, vitamin B12, phenols, flavones, phytosterols, curcumin, blueberry, lipoic acid, catechins, flavonoids, and flavonols, to a human or animal patient in need thereof.

THROMBX™

In certain embodiments, a THROMBX™ composition is a three-component nutritional supplement formulation useful in methods for the prevention and treatment of thrombosis. Blood flow is crucial to health and well being. Thrombosis (blood clotting) interferes with blood flow and contributes to heart attack, stroke, and numerous other disorders. Although conventional drugs address this problem, natural substances are more desirable because (1) they work with the body's own endogenous antithrombotic defense systems (2) they are preventive and can reverse the actual causes of thrombosis and (3) they have limited or no side effects in reasonable doses, which allows for their long-term use. In general, long-term treatment with natural substances is a better alternative than conventional drugs to reverse a chronic, longstanding, and multifactorial condition like thrombosis.

Thrombosis is caused by excess fibrinogen and platelet aggregation. Certain natural substances attack either or both causes. DMSO (and possibly MSM), it is believed, blocks tissue factor (TF) expression and other thrombotic factors. Rutin may work by inhibiting protein disulfide isomerase (PDI), which is a precursor of both platelet aggregation and fibrin production. The mechanisms of action of the flavonoids are varied and less clear, but they include antioxidant effects and upregulation of endothelial nitric oxide, which increases blood flow.

In certain instances, a THROMBX™ composition may contain three components chosen from (1) DMSO, rutin, and one of a flavonoid, DHA, or EPA, or (2) MSM, rutin, and one of a flavonoid, DHA, or EPA. The treatment regimen using THROMBX™ compositions is to take the same or a different three-component formulation at regular intervals during the day. The time intervals are determined by research and testing, in order to reduce, minimize, or eliminate the cancellation effect between such serial administrations. The end result of THROMBX™ composition administration is to maximize the antithrombotic effects of such natural substances with decreased or minimal cancellation effect or interference.

Accordingly, additional embodiments of the present invention provide multi-component pharmaceutical compositions comprising: a compound chosen from methylsulfonylmethane and dimethyl sulfoxide; rutin; and one of docosahexanoic acid (DHA), eicosapentaenoic acid (EPA), and a flavonoid other than rutin.

Some cases provide that the compound is methylsulfonylmethane. Other cases provide that the compound is dimethyl sulfoxide. The compound can be present in any suitable amount. For example, in certain instances, the compound is present in an amount ranging from about 0.01% to about 90% by weight. In other instances, the compound is present in an amount of at least about 0.01%, at least about 0.1%, at least about 0.5%, at least about 1%, at least about 2%, at least about 3%, at least about 4%, at least about 5%, at least about 10%, at least about 20%, or at least about 50% by weight. Still further instances provide that the compound is present in an amount of no more than about 0.1%, no more than about 0.5%, no more than about 1%, no more than about 2%, no more than about 3%, no more than about 4%, no more than about 5%, no more than about 10%, no more than about 20%, no more than about 50%, or no more than about 90% by weight.

Any suitable amount of rutin can be present. In some instances, the rutin is present in an amount ranging from about 0.01% to about 90% by weight. In other instances, the rutin is present in an amount of at least about 1%, at least about 2%, at least about 3%, at least about 4%, at least about 5%, at least about 10%, at least about 20%, or at least about 50% by weight. Still other instances provide the rutin in an amount of no more than about 1%, no more than about 2%, no more than about 3%, no more than about 4%, no more than about 5%, no more than about 10%, no more than about 20%, no more than about 50%, or no more than about 90% by weight.

The component chosen from one of docosahexanoic acid (DHA), eicosapentaenoic acid (EPA), and a flavonoid can be present in any suitable amount. In some cases, the one of docosahexanoic acid (DHA), eicosapentaenoic acid (EPA), and a flavonoid is present in an amount ranging from about 0.01% to about 90% by weight. In other cases, the one of docosahexanoic acid (DHA), eicosapentaenoic acid (EPA), and a flavonoid is present in an amount of at least about 1%, at least about 2%, at least about 3%, at least about 4%, at least about 5%, at least about 10%, at least about 20%, or at least about 50% by weight. Still additional cases provide the one of docosahexanoic acid (DHA), eicosapentaenoic acid (EPA), and a flavonoid in an amount of no more than about 1%, no more than about 2%, no more than about 3%, no more than about 4%, no more than about 5%, no more than about 10%, no more than about 20%, no more than about 50%, or no more than about 90% by weight.

The component chosen from one of docosahexanoic acid (DHA), eicosapentaenoic acid (EPA), and a flavonoid can be present in any suitable form. Sometimes, the composition comprises docosahexanoic acid or a pharmaceutically-acceptable salt thereof, or both. At other times, the composition comprises eicosapentaenoic acid or a pharmaceutically-acceptable salt thereof, or both. Still other times, the composition comprises a flavonoid. Any suitable flavonoid can be used. For example, a flavonoid can be chosen from anthocyanins, purple grape products, red wine extracts, and cranberry.

Yet further embodiments provide methods for treating or preventing thrombosis, one such method comprising administering an effective amount of a multi-component pharmaceutical compositions comprising: a compound chosen from methylsulfonylmethane and dimethyl sulfoxide; rutin; and one of docosahexanoic acid (DHA), eicosapentaenoic acid (EPA), and a flavonoid other than rutin.

The components of such compositions can be present in any suitable amounts. For example, in some cases, the DHA is present in an amount of at least about 1%, at least about 2%, at least about 3%, at least about 4%, at least about 5%, at least about 10%, at least about 20%, or at least about 50% by weight. In other cases, the DHA is present in an amount of no more than about 1%, no more than about 2%, no more than about 3%, no more than about 4%, no more than about 5%, no more than about 10%, no more than about 20%, no more than about 50%, or no more than about 90% by weight. Furthermore, EPA can be present in an amount of at least about 1%, at least about 2%, at least about 3%, at least about 4%, at least about 5%, at least about 10%, at least about 20%, or at least about 50% by weight, for example. For another example, the EPA can be present in an amount of no more than about 1%, no more than about 2%, no more than about 3%, no more than about 4%, no more than about 5%, no more than about 10%, no more than about 20%, no more than about 50%, or no more than about 90% by weight. Moreover, the flavonoid can be present in an amount of at least about 1%, at least about 2%, at least about 3%, at least about 4%, at least about 5%, at least about 10%, at least about 20%, or at least about 50% by weight, for example. Additional examples provide that the flavonoid is present in an amount of no more than about 1%, no more than about 2%, no more than about 3%, no more than about 4%, no more than about 5%, no more than about 10%, no more than about 20%, no more than about 50%, or no more than about 90% by weight.

The three components, furthermore, can be present in any suitable form. Broadly speaking, the components of the present invention can appear in any suitable form, such as, for example, pharmaceutically acceptable salts, hydrates, solvates, crystal forms, and enantiomers. For example, the DHA may comprise a pharmaceutically-acceptable salt thereof. Similarly, the EPA may comprise a pharmaceutically-acceptable salt thereof.

Flow and Glow™

Some embodiments of the present invention provide a FLOW AND GLOW™ composition, which can provide a novel two- or three-component formulation useful in methods for the health and beauty of skin (including lips), hair, and nails. The two components are, in certain instances, methylsulfonylmethane (MSM) and colla corii asini (CCA). The three components are, in certain cases, methylsulfonylmethane (MSM), colla corii asini (CCA), and resveratrol.

CCA is a traditional Chinese medicine derived from donkey skin. It is available in different forms, including glue and powder. CCA has been widely used for a variety of purposes in China for many years, but infrequently in the West, perhaps because of its provenance. CCA comprises numerous amino acids and collagen proteins. When Applicant took CCA, it improved the color, tone, and texture of Applicant's hair and skin, which was observed and commented upon spontaneously by Applicant's hairdresser and then a facialist acquaintance.

MSM is also a small and naturally occurring molecule which is a metabolite of dimethyl sulfoxide (DMSO) in that approximately 15% of DMSO is converted to MSM in the human body. MSM occurs naturally in small amounts in the human body and has extremely low toxicity. MSM is a generally recognized as safe (GRAS) dietary ingredient.

FLOW AND GLOW™ compositions may also be used to prevent or delay both hair loss and graying hair by stimulating blood flow to the scalp and hair follicles. A FLOW AND GLOW™ composition may be administered internally as a pill or by any other method. FLOW AND GLOW™ compositions may also be administered externally as a lotion or by any other topical application to the skin or scalp, including shampoo. MSM is a skin penetrant that may enhance drug delivery through the skin. MSM has also proven to augment intradermal retention and accumulation of topical applications for hair growth.

Accordingly, certain additional embodiments relate to multi-component pharmaceutical compositions comprising: methylsulfonylmethane; colla corii asini; and optionally resveratrol. Some cases provide that the compound is methylsulfonylmethane. The compound can be present in any suitable amount. For example, in certain instances, MSM is present in an amount ranging from about 0.01% to about 90% by weight. In other instances, the compound is present in an amount of at least about 0.01%, at least about 0.1%, at least about 0.5%, at least about 1%, at least about 2%, at least about 3%, at least about 4%, at least about 5%, at least about 10%, at least about 20%, or at least about 50% by weight. Still further instances provide that the compound is present in an amount of no more than about 0.1%, no more than about 0.5%, no more than about 1%, no more than about 2%, no more than about 3%, no more than about 4%, no more than about 5%, no more than about 10%, no more than about 20%, no more than about 50%, or no more than about 90% by weight.

Resveratrol, where present, can appear in any suitable amount. In some cases, the second component is present in an amount ranging from about 0.01% to about 90% by weight. In other cases, the second component is present in an amount of at least about 1%, at least about 2%, at least about 3%, at least about 4%, at least about 5%, at least about 10%, at least about 20%, or at least about 50% by weight. In still other cases, the second component is present in an amount of no more than about 1%, no more than about 2%, no more than about 3%, no more than about 4%, no more than about 5%, no more than about 10%, no more than about 20%, no more than about 50%, or no more than about 90% by weight.

Any suitable colla corii asini can be used in a FLOW AND GLOW™ composition. The colla corii asini can be present in any suitable amount. For example, the colla corii asini can be present in an amount ranging from about 0.01% to about 90% by weight. For another example, the colla corii asini is present in an amount of at least about 1%, at least about 2%, at least about 3%, at least about 4%, at least about 5%, at least about 10%, at least about 20%, or at least about 50% by weight. Still other examples provide that the colla corii asini is present in an amount of no more than about 1%, no more than about 2%, no more than about 3%, no more than about 4%, no more than about 5%, no more than about 10%, no more than about 20%, no more than about 50%, or no more than about 90% by weight.

Further embodiments relate to methods of improving the beauty, appearance, and/or health and the beauty of skin, including lips, hair, nails, or a combination thereof, comprising administering an effective amount of a multi-component pharmaceutical composition comprising methylsulfonylmethane; colla corii asini; and optionally resveratrol, to a human or animal patient in need thereof. Other embodiments relate to methods of improving the health and the beauty of skin, including lips, hair, nails, or a combination thereof comprising administering an effective amount of a multi-component pharmaceutical composition comprising MSM, colla corii asini, and optionally resveratrol, to a human or animal patient in need thereof.

Compositions of the present invention can be made according to any suitable methods. In some cases, the components of a given composition are brought together in a form suitable for administering to a patient. Optionally, one or more carriers or excipients are included, to aid the processing, enhance the physical or chemical properties, or to impart a certain functionality to the composition, such as the inclusion of a foaming agent to build a shampoo composition.

EXAMPLES

Example 1—AUTX™ Composition

Methylsulfonylmethane (250 mg, as dimethyl sulfone, 98%, MilliporeSigma, St. Louis, MO), niacin (500 mg, as nicotinic acid sodium salt, 98%, MilliporeSigma, St. Louis, MO), and eicosapentaenoic acid (530 µL or 500 mg, as cis-5,8,11,14,17-eicosapentaenoic acid, ~90%, MilliporeSigma, St. Louis, MO) are combined and deposited in a gelatin-based soft capsule and sealed, thereby forming an oral dosage AUTX™ composition.

Example 2—ONCX™ Composition

Dimethylsulfoxide (227 µL or 250 mg, 99.9%, MilliporeSigma, St. Louis, MO), curcumin (70 mg, as turmeric extract (BIO-CURCUM®, Arjuna Natural Extracts, India), and wild blueberry powder (500 mg, Allen's Blueberry Freezer, Inc., Ellsworth, ME) are combined and deposited in a gelatin-based soft capsule and sealed, thereby forming an oral dosage ONCX™ composition.

Example 3—THROMBX™ Composition

Methylsulfonylmethane (250 mg, as dimethyl sulfone, 98%, MilliporeSigma, St. Louis, MO), rutin (500 mg, as quercetin-3-rutinoside hydrate, ≥94%, MilliporeSigma, St. Louis, MO), and docosahexanoic acid (500 mg, as docosahexanoic acid single-cell oil, DHASC®, Martek Biosciences Corp., Columbia, MD) are combined and deposited in a gelatin-based soft capsule and sealed, thereby forming an oral dosage THROMBX™ composition.

Example 4—THROMBX™

Methylsulfonylmethane (250 mg, as dimethyl sulfone, 98%, MilliporeSigma, St. Louis, MO), rutin (500 mg, as quercetin-3-rutinoside hydrate, ≥94%, MilliporeSigma, St. Louis, MO), and eicosapentaenoic acid (530 µL or 500 mg, as cis-5,8,11,14,17-eicosapentaenoic acid, ~90%, MilliporeSigma, St. Louis, MO) are combined and deposited in a gelatin-based soft capsule and sealed, thereby forming an oral dosage THROMBX™ composition.

Example 5—FLOW AND GLOW™ Composition

Methylsulfonylmethane (0.1 µM, as dimethyl sulfone, 99.9%) and colla corii asini (50 µg/mL, as Chinese herbal tea, filtered) were combined in water to form a FLOW AND GLOW™ composition. Optionally, resveratrol powder for example, can be added to represent 10% by weight of the composition.

Example 6—Testing DEMX™ Composition Comprising CCA Human Neuron Survival Test Procedure Cryopreserved human stem cell derived neurons obtained from PhoenixSongs Biologicals were thawed and plated at a density of 12,000 cells per well in a 384-well PDL/laminin coated plate. The neurons were maintained in a humidified environment at 37° C. with 5% $CO_2$ for six days with periodic media changes before experimental procedures were performed. The media used for maintenance and dosing was PhoenixSongs Neural Differentiation Medium and for the survival test contained MSM and FDP with final concentrations of 0.1 and 1 µM, respectively. Cells were dosed in triplicate with 10-point dose response curves to determine if there was any protective effect (improved survival of cells) or toxicity with the test compounds versus the untreated cells.

After three-day incubation with test articles, the cells were stained with Hoechst and Propidium Iodide and read on an ArrayScan VTI to determine cell viability. Results were normalized to vehicle. The data shown below are for the composition of Example 6, above.

TABLE 1

| DEMX ™ Composition Neuron Protective Effect | |
| --- | --- |
| CCA Concentration (µg/mL filtered)(with 0.1 µM MSM and 1 µM FDP in water) | Average Cell Viability (Normalized to Viability in Water Vehicle) |
| 100 | 0.952777 |
| 50 | 1.152786 |
| 25 | 0.940228 |
| 12.5 | 0.997506 |
| 6.25 | 0.881642 |
| 3.125 | 0.650454 |
| 1.5625 | 0.941075 |
| 0.78125 | 0.91898 |

TABLE 1-continued

| DEMX ™ Composition Neuron Protective Effect | |
| --- | --- |
| CCA Concentration (µg/mL filtered)(with 0.1 µM MSM and 1 µM FDP in water) | Average Cell Viability (Normalized to Viability in Water Vehicle) |
| 0.390626 | 0.965634 |
| 0.195313 | 0.994104 |

Maximum cell viability occurred at a concentration of colla corii asini of 50 µg/mL.

Similar tests can be performed with the various compositions of the present invention to determine maximum effective concentrations, and then to construct dosing compositions from those tests.

Example 7—Human Neuron Survival Test with Ischemia Challenge

The neurons of Example 6 can face a challenge representing ischemia to test for protective effect by the compositions of the present invention, in the following manner. The neural differentiation medium can be spiked with 5 µM iodoacetic acid. Cells can be dosed with test compositions in triplicate with 10-point dose response curves to determine if the test compositions exhibit any protective effect (improved survival of cells).

Example 8—Primary Chicken Neuron Survival Test Procedure

Primary chicken neurons are obtained as follows. One day old fertilized eggs are stored under appropriate conditions until the start of breeding. On embryonic day zero, eggs are transferred to a breeding incubator and maintained under turning at 37.8° C. and 55% humidity until embryonic day eight.

Neurons are prepared as follows. DIV8 embryos were transferred to plastic dish and decapitated. Both hemispheres are removed, collected, and cleaned from any loose tissue. Hemispheres are then mechanically disassociated and 4.8× $10^4$ cells per well in a 96-well plate, and each well is seeded with 160 µL. The cell culture medium for chicken telencephalon neurons consists of DMEM with 4.5 grams glucose, 5% Nu Serum, 0.01% gentamycin, and 2 mM L-glutamine. Cultures are maintained at 37° C., 95% humidity and 5% $CO_2$.

All cell culture experiments are carried out under sterile conditions and all procedures are performed in a cell culture unit with special cell culture equipment. Glassware, forceps and/or scissors are sterilized prior to experiments. Stock chemical solutions are obtained sterile, and final solution and culture medium are prepared fresh in a laminar airflow cabinet.

Test compositions, such as, for example, vehicle, one ingredient (such as a compound chosen from dimethylsulfoxide and methylsulfonylmethane), two ingredients, such as the compound and one additional substance, and then three ingredients representing embodiments of the present invention disclosed herein, are prepared. Cells are incubated with test compositions at a variety of concentrations of ingredients, for example, from 0.01% to 90% by weight, on DIV8 for 48 hours until DIV10, when cell viability can be determined according to MTT assay. MTT assay uses a plate reader at 570 nanometers as described in SOP MET004. The assay measures the mitochondrial dehydrogenase activity which reduces yellow MTT to dark blue formazan crystals. As the reaction is catalyzed only in living cells, the assay is used to determine cell viability. MTT is added to each well at a concentration of 0.5 milligrams per milliliter. After two hours, the MTT containing medium is aspirated. Cells are lysed in 3% SDS and the formazan crystals are dissolved in isopropanol/hydrochloric acid. Optical density is measured with a plate-reader at a wavelength of 570 nanometers. Cell survival rate is expressed as optical density, and values are calculated as a percentage of the vehicle control values, the vehicle control being 100%. Statistical significance can be determined by One-Way ANOVA (Newman-Keuls Multiple Comparison Test). Data can be shown from two independent experiments as a percent cell viability compared to vehicle-treated cells or two-ingredient compositions.

Example 9—Alzheimer Disease Model Protective Effects

Transgenic Animals: Test are conducted on female transgenic mice with the Swedish and the London mutations over-expressing human amyloid precursor protein (hAPP (751)) ($APP_{SL}$) under the control of the murine Thy-1 promoter with a C57BL/6×DBA background are utilized. The mice are tested in two groups, a placebo group (no test formulation) (n=18) and an experimental group (with the test formulation) (n=18). The mice utilized are at 6 months of age (±2 weeks) at the start of the study.

Delivery Of Experimental Test Formulation To Test Animals: Standard rodent chow (SSNIFF® R/M, 10 mm) and normal tap water are utilized to deliver the test formulations to the transgenic animals daily. In the placebo group, normal rat chow and tap water are utilized, minus the formulation components.

Timeframe Of Study: The study is performed for 6 months, wherein the test animals receive either a daily dosages of the test formulation, or the placebo, after which, behavioral and further analyses performed.

Morris Water Maze Behavioral Analysis: The Morris water maze ("MWM") test is a spatial navigation test to evaluate learning and memory. Training in the MWM takes place at the end of the treatment. The MWM consists of a white circular pool of a diameter of 100 cm, filled with tap water at a temperature of 21±2° C. The pool is virtually divided into four sectors. A transparent platform (8 cm diameter) is placed about 0.5 cm beneath the water surface. During all test sessions, except the pretest, the platform is located in the southwest quadrant of the pool.

Each mouse must perform three trials on each of four consecutive days. A single trial lasts for a maximum of one minute. During this time, the mouse has the chance to find the hidden, diaphanous target. After each trial mice are allowed to rest on the platform for 10-15 sec to orientate in the surrounding.

At least one hour after the last trial on day 4, mice have to fulfill a so-called probe trial. During the probe trial, the platform is removed from the pool and the number of crossings over the former target position is recorded together with the abidance in this quadrant.

For the quantification of escape latency (the time [in seconds] the mouse needs to find the hidden platform and to escape from the water), of pathway (the length of the trajectory [in meters] to reach the target) and of the abidance in the goal quadrant in the probe trial, a computerized tracking system is used. All animals have to perform a visual test after the probe trial on the last day to exclude influence of impaired visual abilities on behavioral results.

Contextual Fear Conditioning Of Mice: Fear conditioning is conducted in an automated box (TSE-Systems, Germany). Mice are trained and tested on 2 consecutive days. On the training day, 10 minutes after treatment, mice receive a footshock (0.5 mA, 2 s) 5 seconds after being placed into the conditioning chamber. After 30 seconds, the mice are returned to their original cage.

Twenty-four hours after training, mice are tested by being returned to the conditioning chamber for 5 minutes without any shock, and the freezing behavior is recorded by the automated system and evaluated separately every minute. Freezing is defined as a lack of movement, except for movement that is required for respiration.

Tissue Sampling: After 6 months of treatment and finishing all behavioral tasks, animals are sacrificed and blood, cerebrospinal fluid ("CSF"), and brains collected. CSF is obtained by blunt dissection and exposure of the foramen magnum. Upon exposure, a Pasteur pipette is inserted to the approximate depth of 0.3-1 mm into the foramen magnum. CSF is collected by suction and capillary action until flow fully ceases. Samples are immediately frozen on dry ice and stored at −80° C. until used for Aβ determination.

After CSF sampling, each mouse is placed in the dorsal position, the thorax is opened and a 26-gauge needle attached to a 1 cc syringe inserted into the right cardiac ventricular chamber. Blood is then collected into ethylenediaminetetraacetic acid ("EDTA") coated vials and consequently used to obtain plasma. To get plasma, blood samples from each mouse (in EDTA coated vials) is centrifuged (1000×g, 10 minutes, room temperature). Plasma (supernatant) is frozen in aliquots until used for Aβ determination.

Following blood sampling, mice are transcardially perfused with physiological (0.9%) saline. Thereafter, brains removed, cerebellum cut off and frozen, and hemispheres divided. The left hemisphere is used for biochemical analysis; the right hemisphere is fixed and used for histological investigations.

Brain Protein Extraction: After dividing the brain hemispheres of each mouse, the left hemisphere sample without the cerebellum is homogenized and separated into 4 fractions: TBS, Triton X-100, SDS, and FA.

After thawing, the hemispheres are homogenized with a Homogenizer "Ultra Turrax T8" at highest speed in TBS (20 mM Tris, 137 mM NaCl, pH=7.6; containing protease inhibitor cocktail; 100 mg brain wet weight per mL TBS). One aliquot (1 mL) is centrifuged (74,200×g for 1 h at 4° C.) and the supernatants stored at −20° C. (TBS fraction). The pellets are suspended in 1 mL Triton X-100 (1% in TBS), centrifuged as above, and the supernatants kept at −20° C. (Triton X-100 fraction). The pellets are suspended in 1 mL SDS (2% SDS in aqua bidest), centrifuged as above, and the supernatants kept at −20° C. (SDS fraction). The pellets out of the SDS fraction are suspended in 0.5 mL formic acid (70% in aqua bidest) prior to subsequent centrifugation (as above). The supernatants are neutralized with 9.5 mL TRIS (1M in aqua bidest) and kept at −20° C. (FA fraction). All four fractions are used for Aβ38, Aβ40 and Aβ42 determination.

It can be assumed that TBS and Triton X-100 solubilize monomeric to oligomeric structures. Polymers like protofibrils and water insoluble fibrils can be resolved in SDS and FA. The investigation of all four fractions provides data also about the Aβ polymerization status.

Aβ Level Determination: Aβ38, Aβ40 and Aβ42 levels are measured in the four different brain homogenate fractions (TBS, Triton X-100, SDS and FA) and in CSF of each transgenic mouse with a commercially available Aβ-kit (Mesoscale Discovery). Samples from the brain preparations are analyzed in duplicate. Due to the small amount, CSF samples are analyzed only once. Aβ levels are evaluated in comparison to peptide standards as nanogram Aβ per gram brain or nanogram Aβ per mL CSF.

Tissue Fixation, Preparation And Sectioning: The right hemispheres of the mice are fixed by immersion in a freshly produced 4% solution of paraformaldehyde/PBS (pH 7.4) for one hour at room temperature. Thereafter, brains are transferred to a 15% sucrose PBS solution for 24 hours to ensure cryoprotection. The following day, brains are frozen in isopentane and stored at −80° C. until used for histological analysis.

The immersion-fixed and cryoprotected frozen right hemispheres are used to prepare sagittal cryosections (10 μm thickness) for histological analysis on a Leica CM 3050S cryotome. Collection of sections starts at a level approximately 0.24 mm lateral from midline and extends through the hemisphere, usually resulting in collecting sections from 12 medio-lateral levels in order to cover the entire cortex and hippocampus.

Sections are stored at −20° C. until used in immunohistochemistry (IHC). Systematic random sets of sections (5 slices from 5 levels) are histologically investigated for 6E10 and ThioflavinS labeling, CD11b/GFAP and AT180 IHC using multi-channel fluorescence.

Determination Of Plaque Load: Plaque load is quantified by staining with 6E10 IHC directed against AA1-16 of the human amyloid peptide and ThioflavinS staining against beta-sheet structures in a double incubation. Region areas (hippocampus and cortex) are measured and plaque surface area and number of plaques per region area measured and counted using automated image analysis software (Image ProPlus, version 6.2).

Determination Of Inflammation: Astrocytes are evaluated using a rabbit anti-Glial Fibrillary Acidic Protein (DAKO®) antibody. Microglia is detected by a mouse anti-murine CD11b (SEROTEC®) antibody. Region areas (hippocampus and cortex) are measured and the percentage of GFAP (astrocytes) and CD11b immunoreactivity area (microglia) per region area are measured and counted using automated image analysis software (Image ProPlus, version 6.2).

Determination of Phosphorylated Tau: Tau phosphorylation (pTau) around plaques is visualized immunohistochemically using an AT180 antibody. Clone AT180 recognizes PHF-Tau double-phosphorylated at Thr231 and Ser235.

Additional Evaluations: All remaining tissues from the mice are stored and used for later determination of neuroprotective proteins and epigenetic factors that might also play a role in AD. Statistical Analyses: Descriptive statistical analysis is performed on all measured parameters. Data is represented as mean±standard deviation (SD) or standard error of mean (SEM). In case of differences between groups, appropriate basic statistical tests (one-way ANOVA, T-test, etc.) are performed.

EMBODIMENTS

Embodiment 1. A multi-component pharmaceutical composition comprising:
methylsulfonylmethane;
vitamin B3; and
a natural substance.

Embodiment 2. The multi-component pharmaceutical composition of embodiment 1, wherein the methylsulfonylmethane is present in an amount ranging from about 0.01% to about 90% by weight.

Embodiment 3. The multi-component pharmaceutical composition of any one of embodiments 1-2, wherein the methylsulfonylmethane is present in an amount of at least about 0.01%, at least about 0.1%, at least about 0.5%, at least about 1%, at least about 2%, at least about 3%, at least about 4%, at least about 5%, at least about 10%, at least about 20%, or at least about 50% by weight.

Embodiment 4. The multi-component pharmaceutical composition of any one of embodiments 1-3, wherein the methylsulfonylmethane is present in an amount of no more than about 0.1%, no more than about 0.5%, no more than about 1%, no more than about 2%, no more than about 3%, no more than about 4%, no more than about 5%, no more than about 10%, no more than about 20%, no more than about 50%, or no more than about 90% by weight.

Embodiment 5. The multi-component pharmaceutical composition of any one of embodiments 1-4, wherein the vitamin B3 is present as niacin, niacinamide, or niacinamide riboside.

Embodiment 6. The multi-component pharmaceutical composition of any one of embodiments 1-5, wherein the vitamin B3 is present in an amount ranging from about 0.01% to about 90% by weight.

Embodiment 7. The multi-component pharmaceutical composition of any one of embodiments 1-6, wherein the vitamin B3 is present in an amount of at least about 1%, at least about 2%, at least about 3%, at least about 4%, at least about 5%, at least about 10%, at least about 20%, or at least about 50% by weight.

Embodiment 8. The multi-component pharmaceutical composition of any one of embodiments 1-7, wherein the vitamin B3 is present in an amount of no more than about 1%, no more than about 2%, no more than about 3%, no more than about 4%, no more than about 5%, no more than about 10%, no more than about 20%, no more than about 50%, or no more than about 90% by weight.

Embodiment 9. The multi-component pharmaceutical composition of any one of embodiments 1-8, wherein the natural substance is one of ashwagandha, curcumin, resveratrol, green tea, rutin, vitamin D, docosahexanoic acid (DHA), eicosapentaenoic acid (EPA), pomegranate, quercetin, and cocoa.

Embodiment 10. The multi-component pharmaceutical composition of any one of embodiments 1-9, wherein the natural substance is present in an amount ranging from about 0.01% to about 90% by weight.

Embodiment 11. The multi-component pharmaceutical composition of any one of embodiments 1-10, wherein the natural substance is present in an amount of at least about 1%, at least about 2%, at least about 3%, at least about 4%, at least about 5%, at least about 10%, at least about 20%, or at least about 50% by weight.

Embodiment 12. The multi-component pharmaceutical composition of any one of embodiments 1-11, wherein the natural substance is present in an amount of no more than about 1%, no more than about 2%, no more than about 3%, no more than about 4%, no more than about 5%, no more than about 10%, no more than about 20%, no more than about 50%, or no more than about 90% by weight.

Embodiment 13. A method of preventing or treating an autoimmune disease or disorder, comprising administering an effective amount of the multi-component pharmaceutical composition of any one of embodiments 1-12 to a human or animal patient in need thereof.

Embodiment 14. A method of reducing a risk of autism spectrum disorder in a child of a female patient, comprising administering to the female patient an effective amount of the multi-component pharmaceutical composition of any one of embodiments 1-13, before the female patient becomes pregnant with the child.

Embodiment 15. A multi-component pharmaceutical composition comprising:

three substances chosen from methylsulfonylmethane, dimethyl sulfoxide, selenium, zinc, garlic, *ginseng*, probiotics, astralagus, *echinacea*, olive leaf, ashwagandha, rutin, vitamin A, vitamin B3 vitamin C, vitamin E, folic acid, vitamin B6, vitamin B12, phenols, flavones, phytosterols, curcumin, blueberry, lipoic acid, resveratrol, green tea, vitamin D, docosahexanoic acid (DHA), eicosapentaenoic acid (EPA), pomegranate, quercetin, cocoa, catechins, flavonoids, and flavonols.

Embodiment 16. A multi-component pharmaceutical composition comprising:

three substances chosen from alfalfa, barley grass, blessed thistle, cauliflower, *chlorella*, cilantro, dandelion, flax seed, Japanese knotweed, kelp, lemon balm, lemon grass, nettle, plantain, sunflower seed, Siberian eleuthero, wheat grass, *spirulina*, blue green algae extract, açaí, apple, asparagus, banana, beet, blueberry, broccoli, brussels sprout, cabbage, carrot, cranberry, cucumber, grape, grapefruit, hawthorn berry, lemon, lime, orange, pea, pear, pineapple, plum, pomegranate, pumpkin, raspberry, spinach, strawberry, tangerine, tart cherry, tomato, alpha galactosidase, amylase, bromelain, cellulase, coenzyme Q10, invertase, lactase, lipase, papain, peptidases, protease I, protease II, agarikon (lariciformes *officinalis* and fomitopsis *officinalis*), chaga (inonotus obliquus), enokitake (flammulina velutipes), himematsutake (*agaricus brasiliensis, agaricus* blazei), kawaratake (*trametes versicolor*), maitake (grifola *frondosa*), mesima (*phellinus* linteus), oyster hirotaka (*pleurotus* ostreatus), reishi (*Ganoderma lucidum*), shiitake (*lentinula edodes*), yamabushitake (hericium *erinaceus*), Zhu Ling (grifola *umbellata*), betaine HCl, choline, eriocitrin, fructose diphosphate (FDP), hesperidin, inositol, naringin, narirutin, resveratrol, rutin, lutein, calcium, copper, iodine, iron, magnesium, manganese, molybdenum, potassium, selenium, sodium, and zinc, vitamin A (as beta carotene and/or retinyl acetate, for example), vitamin B3 (niacin, nicotinamide, and/or nicotinamide riboside), vitamin B6, vitamin B12, vitamin C, vitamin D3, vitamin E, vitamin K1, riboflavin, biotin, folic acid, pantothenic acid, and thiamine.

Embodiment 17. The multi-component pharmaceutical composition of any one of embodiments 15-16, wherein the composition does not include vitamin B3.

Embodiment 18. The multi-component pharmaceutical composition of any one of embodiments 15-17, wherein the composition does not include rutin.

Embodiment 19. The multi-component pharmaceutical composition of any one of embodiments 15-18, wherein the composition does not include fructose 1,6-diphosphate.

Embodiment 20. The multi-component pharmaceutical composition of any one of embodiments 15-19, comprising methylsulfonylmethane.

Embodiment 21. The multi-component pharmaceutical composition of any one of embodiments 15-20, comprising dimethyl sulfoxide.

Embodiment 22. The multi-component pharmaceutical composition of any one of embodiments 15-21, wherein one of the three substances is present in an amount ranging from about 0.01% to about 90% by weight.

Embodiment 23. The multi-component pharmaceutical composition of any one of embodiments 15-22, wherein one of the three substances is present in an amount of at least about 0.01%, at least about 0.1%, at least about 0.5%, at least about 1%, at least about 2%, at least about 3%, at least about 4%, at least about 5%, at least about 10%, at least about 20%, or at least about 50% by weight.

Embodiment 24. The multi-component pharmaceutical composition of any one of embodiments 15-23, wherein one of the three substances is present in an amount of no more than about 0.1%, no more than about 0.5%, no more than about 1%, no more than about 2%, no more than about 3%, no more than about 4%, no more than about 5%, no more than about 10%, no more than about 20%, no more than about 50%, or no more than about 90% by weight.

Embodiment 25. The multi-component pharmaceutical composition of any one of embodiments 15-24, wherein the flavonoids are chosen from anthocyanins, purple grape products, red wine extract, and cranberry.

Embodiment 26. The multi-component pharmaceutical composition of any one of embodiments 15-25, wherein the three substances are chosen from selenium, zinc, garlic, *ginseng*, astralagus, *echinacea*, olive leaf, ashwagandha, rutin, vitamin A, vitamin B3, vitamin C, vitamin E, folic acid, vitamin B6, vitamin B12, curcumin, blueberry, lipoic acid, anthocyanins, purple grape products, red wine extract, and cranberry.

Embodiment 27. The multi-component pharmaceutical composition of any one of embodiments 15-26, wherein the three substances are present in an amount ranging from about 0.02% to about 90% by weight.

Embodiment 28. The multi-component pharmaceutical composition of any one of embodiments 15-27, wherein the three substances are present in an amount of at least about 1%, at least about 2%, at least about 3%, at least about 4%, at least about 5%, at least about 10%, at least about 20%, or at least about 50% by weight.

Embodiment 29. The multi-component pharmaceutical composition of any one of embodiments 15-28, wherein the three substances are present in an amount of no more than about 1%, no more than about 2%, no more than about 3%, no more than about 4%, no more than about 5%, no more than about 10%, no more than about 20%, no more than about 50%, or no more than about 90% by weight.

Embodiment 30. A multi-component pharmaceutical composition comprising:

three substances chosen from methylsulfonylmethane, vitamin B3, rutin, selenium, zinc, garlic, *ginseng*, probiotics, astralagus, *echinacea*, olive leaf, ashwagandha, vitamin A, vitamin C, vitamin E, folic acid, vitamin B6, vitamin B12, phenols, flavones, phytosterols, curcumin, blueberry, lipoic acid, resveratrol, green tea, vitamin D, docosahexanoic acid (DHA), eicosapentaenoic acid (EPA), pomegranate, quercetin, cocoa, catechins, anthocyanins, purple grape products, red wine extract, cranberry, flavonoids, and flavonols.

Embodiment 31. A method of treating or preventing cancer, comprising administering an effective amount of the multi-component pharmaceutical composition of any one of embodiments 15-30 to a human or animal patient in need thereof.

Embodiment 32. A multi-component pharmaceutical composition comprising:
methylsulfonylmethane;
rutin; and
one of docosahexanoic acid (DHA), eicosapentaenoic acid (EPA), and a flavonoid other than rutin.

Embodiment 33. The multi-component pharmaceutical composition of embodiment 32, wherein the methylsulfonylmethane is present in an amount ranging from about 0.01% to about 90% by weight.

Embodiment 34. The multi-component pharmaceutical composition of any one of embodiments 32-33, wherein the methylsulfonylmethane is present in an amount of at least about 0.01%, at least about 0.1%, at least about 0.5%, at least about 1%, at least about 2%, at least about 3%, at least about 4%, at least about 5%, at least about 10%, at least about 20%, or at least about 50% by weight.

Embodiment 35. The multi-component pharmaceutical composition of any one of embodiments 32-34, wherein the methylsulfonylmethane is present in an amount of no more than about 0.1%, no more than about 0.5%, no more than about 1%, no more than about 2%, no more than about 3%, no more than about 4%, no more than about 5%, no more than about 10%, no more than about 20%, no more than about 50%, or no more than about 90% by weight.

Embodiment 36. The multi-component pharmaceutical composition of any one of embodiments 32-35, wherein the rutin is present in an amount ranging from about 0.01% to about 90% by weight.

Embodiment 37. The multi-component pharmaceutical composition of any one of embodiments 32-36, wherein the rutin is present in an amount of at least about 1%, at least about 2%, at least about 3%, at least about 4%, at least about 5%, at least about 10%, at least about 20%, or at least about 50% by weight.

Embodiment 38. The multi-component pharmaceutical composition of any one of embodiments 32-37, wherein the rutin is present in an amount of no more than about 1%, no more than about 2%, no more than about 3%, no more than about 4%, no more than about 5%, no more than about 10%, no more than about 20%, no more than about 50%, or no more than about 90% by weight.

Embodiment 39. The multi-component pharmaceutical composition of any one of embodiments 32-38, wherein the one of docosahexanoic acid (DHA), eicosapentaenoic acid (EPA), and a flavonoid is present in an amount ranging from about 0.01% to about 90% by weight.

Embodiment 40. The multi-component pharmaceutical composition of any one of embodiments 32-39, wherein the one of docosahexanoic acid (DHA), eicosapentaenoic acid (EPA), and a flavonoid is present in an amount of at least about 1%, at least about 2%, at least about 3%, at least about 4%, at least about 5%, at least about 10%, at least about 20%, or at least about 50% by weight.

Embodiment 41. The multi-component pharmaceutical composition of any one of embodiments 32-40, wherein the one of docosahexanoic acid (DHA), eicosapentaenoic acid (EPA), and a flavonoid is present in an amount of no more than about 1%, no more than about 2%, no more than about 3%, no more than about 4%, no more than about 5%, no more than about 10%, no more than about 20%, no more than about 50%, or no more than about 90% by weight.

Embodiment 42. The multi-component pharmaceutical composition of any one of embodiments 32-41, wherein the one of docosahexanoic acid (DHA), eicosapentaenoic acid (EPA), and a flavonoid is docosahexanoic acid (DHA) or a pharmaceutically-acceptable salt thereof.

Embodiment 43. The multi-component pharmaceutical composition of any one of embodiments 32-42, wherein the one of docosahexanoic acid (DHA), eicosapentaenoic acid (EPA), and a flavonoid is eicosapentaenoic acid or a pharmaceutically-acceptable salt thereof.

Embodiment 44. The multi-component pharmaceutical composition of any one of embodiments 32-43, wherein the one of docosahexanoic acid (DHA), eicosapentaenoic acid (EPA), and a flavonoid is a flavonoid.

Embodiment 45. The multi-component pharmaceutical composition of any one of embodiments 32-44, wherein the one of docosahexanoic acid (DHA), eicosapentaenoic acid (EPA), and a flavonoid is a flavonoid chosen from anthocyanins, purple grape products, red wine extracts, and cranberry.

Embodiment 46. The multi-component pharmaceutical composition of embodiment 42, wherein DHA is present in an amount of at least about 1%, at least about 2%, at least about 3%, at least about 4%, at least about 5%, at least about 10%, at least about 20%, or at least about 50% by weight.

Embodiment 47. The multi-component pharmaceutical composition of embodiment 42, wherein DHA is present in an amount of no more than about 1%, no more than about 2%, no more than about 3%, no more than about 4%, no more than about 5%, no more than about 10%, no more than about 20%, no more than about 50%, or no more than about 90% by weight.

Embodiment 48. The multi-component pharmaceutical composition of embodiment 43, wherein EPA is present in an amount of at least about 1%, at least about 2%, at least about 3%, at least about 4%, at least about 5%, at least about 10%, at least about 20%, or at least about 50% by weight.

Embodiment 49. The multi-component pharmaceutical composition of embodiment 43, wherein EPA is present in an amount of no more than about 1%, no more than about 2%, no more than about 3%, no more than about 4%, no more than about 5%, no more than about 10%, no more than about 20%, no more than about 50%, or no more than about 90% by weight.

Embodiment 50. The multi-component pharmaceutical composition of embodiment 44, wherein the flavonoid is present in an amount of at least about 1%, at least about 2%, at least about 3%, at least about 4%, at least about 5%, at least about 10%, at least about 20%, or at least about 50% by weight.

Embodiment 51. The multi-component pharmaceutical composition of embodiment 44, wherein the flavonoid is present in an amount of no more than about 1%, no more than about 2%, no more than about 3%, no more than about 4%, no more than about 5%, no more than about 10%, no more than about 20%, no more than about 50%, or no more than about 90% by weight.

Embodiment 52. The multi-component pharmaceutical composition of any one of embodiments 32-51, wherein the DHA comprises a pharmaceutically-acceptable salt thereof.

Embodiment 53. The multi-component pharmaceutical composition of any one of embodiments 32-52, wherein the EPA comprises a pharmaceutically-acceptable salt thereof.

Embodiment 54. A method of treating or preventing thrombosis, comprising administering an effective amount of the multi-component pharmaceutical composition of any one of embodiments 32-53 to a human or animal patient in need thereof.

Embodiment 55. A multi-component pharmaceutical composition comprising:
methylsulfonylmethane;
colla corii asini;
and optionally resveratrol.

Embodiment 56. The multi-component pharmaceutical composition of embodiment 55, wherein the methylsulfonylmethane is present in an amount ranging from about 0.01% to about 90% by weight.

Embodiment 57. The multi-component pharmaceutical composition of any one of embodiments 55-56, wherein the methylsulfonylmethane is present in an amount of at least about 0.01%, at least about 0.1%, at least about 0.5%, at least about 1%, at least about 2%, at least about 3%, at least about 4%, at least about 5%, at least about 10%, at least about 20%, or at least about 50% by weight.

Embodiment 58. The multi-component pharmaceutical composition of any one of embodiments 55-57, wherein the methylsulfonylmethane is present in an amount of no more than about 0.1%, no more than about 0.5%, no more than about 1%, no more than about 2%, no more than about 3%, no more than about 4%, no more than about 5%, no more than about 10%, no more than about 20%, no more than about 50%, or no more than about 90% by weight.

Embodiment 59. The multi-component pharmaceutical composition of any one of embodiments 55-58, wherein the resveratrol is present in an amount ranging from about 0.01% to about 90% by weight.

Embodiment 60. The multi-component pharmaceutical composition of any one of embodiments 55-59, wherein the resveratrol is present in an amount of at least about 1%, at least about 2%, at least about 3%, at least about 4%, at least about 5%, at least about 10%, at least about 20%, or at least about 50% by weight.

Embodiment 61. The multi-component pharmaceutical composition of any one of embodiments 55-60, wherein the resveratrol is present in an amount of no more than about 1%, no more than about 2%, no more than about 3%, no more than about 4%, no more than about 5%, no more than about 10%, no more than about 20%, no more than about 50%, or no more than about 90% by weight.

Embodiment 62. The multi-component pharmaceutical composition of any one of embodiments 55-61, wherein the colla corii asini is present in an amount ranging from about 0.01% to about 90% by weight.

Embodiment 63. The multi-component pharmaceutical composition of any one of embodiments 55-62, wherein the colla corii asini is present in an amount of at least about 1%, at least about 2%, at least about 3%, at least about 4%, at least about 5%, at least about 10%, at least about 20%, or at least about 50% by weight.

Embodiment 64. The multi-component pharmaceutical composition of any one of embodiments 55-63, wherein the colla corii asini is present in an amount of no more than about 1%, no more than about 2%, no more than about 3%, no more than about 4%, no more than about 5%, no more than about 10%, no more than about 20%, no more than about 50%, or no more than about 90% by weight.

Embodiment 65. A method of improving the beauty, appearance, and/or health of skin, lips, hair, nails, or a combination thereof, comprising administering an effective amount of the multi-component pharmaceutical composition of any one of embodiments 55-64 to a human or animal patient in need thereof.

Embodiment 66. A multi-component pharmaceutical composition consisting essentially of:
methylsulfonylmethane;
fructose diphosphate (FDP); and
an herbal component or a nutritional component;
wherein the composition does not contain docosahexanoic acid (DHA), resveratrol, blueberry, curcumin, trehalose, green tea extract, ashwagandha, or rutin.

Embodiment 67. The multi-component pharmaceutical composition of embodiment 66, wherein the methylsulfonylmethane is present in an amount ranging from about 0.01% to about 90% by weight.

Embodiment 68. The multi-component pharmaceutical composition of any one of embodiments 66-67, wherein the methylsulfonylmethane is present in an amount of at least about 0.01%, at least about 0.1%, at least about 0.5%, at least about 1%, at least about 2%, at least about 3%, at least about 4%, at least about 5%, at least about 10%, at least about 20%, or at least about 50% by weight.

Embodiment 69. The multi-component pharmaceutical composition of any one of embodiments 66-68, wherein the methylsulfonylmethane is present in an amount of no more than about 0.1%, no more than about 0.5%, no more than about 1%, no more than about 2%, no more than about 3%, no more than about 4%, no more than about 5%, no more than about 10%, no more than about 20%, no more than about 50%, or no more than about 90% by weight.

Embodiment 70. The multi-component pharmaceutical composition of any one of embodiments 66-69, wherein the fructose diphosphate (FDP) is present in an amount ranging from about 0.01% to about 90% by weight.

Embodiment 71. The multi-component pharmaceutical composition of any one of embodiments 66-70, wherein the fructose diphosphate (FDP) is present in an amount of at least about 1%, at least about 2%, at least about 3%, at least about 4%, at least about 5%, at least about 10%, at least about 20%, or at least about 50% by weight.

Embodiment 72. The multi-component pharmaceutical composition of any one of embodiments 66-71, wherein the fructose diphosphate (FDP) is present in an amount of no more than about 1%, no more than about 2%, no more than about 3%, no more than about 4%, no more than about 5%, no more than about 10%, no more than about 20%, no more than about 50%, or no more than about 90% by weight.

Embodiment 73. The multi-component pharmaceutical composition of any one of embodiments 66-72, wherein the one or more of an herbal component, a nutritional component, or a combination thereof is one of alfalfa, barley grass, blessed thistle, cauliflower, *chlorella*, cilantro, dandelion, flax seed, Japanese knotweed, kelp, lemon balm, lemon grass, nettle, plantain, sunflower seed, Siberian eleuthero, wheat grass, *spirulina*, blue green algae extract, açaí, apple, asparagus, banana, beet, blueberry, broccoli, brussels sprout, cabbage, carrot, cranberry, cucumber, grape, grapefruit, hawthorn berry, lemon, lime, orange, pea, pear, pineapple, plum, pomegranate, pumpkin, raspberry, spinach, strawberry, tangerine, tart cherry, tomato, alpha galactosidase, amylase, bromelain, cellulase, coenzyme Q10, invertase, lactase, lipase, papain, peptidases, protease I, protease II, agarikon (laricifomes *officinalis* and fomitopsis *officinalis*), chaga (inonotus obliquus), enokitake (flammulina velutipes), himematsutake (*agaricus brasiliensis, agaricus* blazei), kawaratake (*trametes versicolor*), maitake (grifola *frondosa*), mesima (*phellinus* linteus), oyster hirotaka (*pleurotus* ostreatus), reishi (*Ganoderma lucidum*), shiitake (*lentinula edodes*), yamabushitake (hericium erinaceus), Zhu Ling (grifola *umbellata*), betaine HCl, choline, eriocitrin, fructose diphosphate (FDP), hesperidin, inositol, naringin, narirutin, resveratrol, rutin, lutein, calcium, copper, iodine, iron, magnesium, manganese, molybdenum, potassium, selenium, sodium, and zinc, vitamin A (as beta carotene and/or retinyl acetate, for example), vitamin B3 (niacin, nicotinamide, and/or nicotinamide riboside), vitamin B6, vitamin B12, vitamin C, vitamin D3, vitamin E, vitamin K1, riboflavin, biotin, folic acid, pantothenic acid, quercetin, or thiamine.

Embodiment 74. The multi-component pharmaceutical composition of any one of embodiments 66-73, wherein the one or more of an herbal component, a nutritional component, or a combination thereof is present in an amount ranging from about 0.01% to about 90% by weight.

Embodiment 75. The multi-component pharmaceutical composition of any one of embodiments 66-74, wherein the one or more of an herbal component, a nutritional component, or a combination thereof is present in an amount of at least about 1%, at least about 2%, at least about 3%, at least about 4%, at least about 5%, at least about 10%, at least about 20%, or at least about 50% by weight.

Embodiment 76. The multi-component pharmaceutical composition of any one of embodiments 66-75, wherein the one or more of an herbal component, a nutritional component, or a combination thereof is present in an amount of no more than about 1%, no more than about 2%, no more than about 3%, no more than about 4%, no more than about 5%, no more than about 10%, no more than about 20%, no more than about 50%, or no more than about 90% by weight.

Embodiment 77. A multi-component pharmaceutical composition consisting essentially of:
methylsulfonylmethane in an amount greater than about 5.0% by weight; fructose diphosphate (FDP); and
a third component chosen from one of docosahexanoic acid (DHA), resveratrol, blueberry, curcumin, trehalose, green tea extract, ashwagandha, and rutin.

Embodiment 78. The multi-component pharmaceutical composition of embodiment 77, wherein the methylsulfonylmethane is present in an amount ranging from greater than about 5.0% to about 90% by weight.

Embodiment 79. The multi-component pharmaceutical composition of any one of embodiments 77-78, wherein the methylsulfonylmethane is present in an amount of at least about 10%, at least about 20%, or at least about 50% by weight.

Embodiment 80. The multi-component pharmaceutical composition of any one of embodiments 77-79, wherein the methylsulfonylmethane is present in an amount of no more than about 10%, no more than about 20%, no more than about 50%, or no more than about 90% by weight.

Embodiment 81. The multi-component pharmaceutical composition of any one of embodiments 77-80, wherein the fructose diphosphate (FDP) is present in an amount ranging from about 0.01% to about 90% by weight.

Embodiment 82. The multi-component pharmaceutical composition of any one of embodiments 77-81, wherein the fructose diphosphate (FDP) is present in an amount of at least about 1%, at least about 2%, at least about 3%, at least about 4%, at least about 5%, at least about 10%, at least about 20%, or at least about 50% by weight.

Embodiment 83. The multi-component pharmaceutical composition of any one of embodiments 77-82, wherein the fructose diphosphate (FDP) is present in an amount of no more than about 1%, no more than about 2%, no more than about 3%, no more than about 4%, no more than about 5%, no more than about 10%, no more than about 20%, no more than about 50%, or no more than about 90% by weight.

Embodiment 84. The multi-component pharmaceutical composition of any one of embodiments 77-83, wherein the third component is present in an amount ranging from about 0.01% to about 90% by weight.

Embodiment 85. The multi-component pharmaceutical composition of any one of embodiments 77-84, wherein the third component is present in an amount of at least about 1%, at least about 2%, at least about 3%, at least about 4%, at least about 5%, at least about 10%, at least about 20%, or at least about 50% by weight.

Embodiment 86. The multi-component pharmaceutical composition of any one of embodiments 77-85, wherein the third component is present in an amount of no more than about 1%, no more than about 2%, no more than about 3%, no more than about 4%, no more than about 5%, no more than about 10%, no more than about 20%, no more than about 50%, or no more than about 90% by weight.

Embodiment 87. A method for administering multi-component pharmaceutical compositions to a human patient in need thereof, comprising:
administering to the patient a first multi-component pharmaceutical composition consisting essentially of three or more first components at a first time of day; and
administering to the patient a second multi-component pharmaceutical composition consisting essentially of three or more second components at a second time of day,
wherein at least one of the three or more first components is different than at least one of the three or more second components.

Embodiment 88. The method of embodiment 87, wherein the first multi-component pharmaceutical composition is present in a first form, and the second multi-component pharmaceutical composition is present in a second form, and the first form differs from the second form by phase, shape, color, size, name, number of dosage forms, packaging, or a combination thereof.

Embodiment 89. The method of embodiment 87, wherein the first form is chosen from a tablet, pill, lozenge, dragee, troche, hard or soft capsule, powder, cachet, granule, suppository, solution, aqueous or oily suspension, emulsion, lotion, syrup, ointment, gel, paste, cream, foam, vapor, spray, aerosol, and transdermal patch.

Embodiment 90. The method of any one of embodiments 88-89, wherein the second form is chosen from a tablet, pill, lozenge, dragee, troche, hard or soft capsule, powder, cachet, granule, suppository, solution, aqueous or oily suspension, emulsion, lotion, syrup, ointment, gel, paste, cream, foam, vapor, spray, aerosol, and transdermal patch.

Embodiment 91. The method of any one of embodiments 87-90, wherein the first multi-component pharmaceutical composition comprises any one of the multi-component pharmaceutical compositions of embodiments 1-12, 15-30, 32-53, 55-64, and 66-86.

Embodiment 92. The method of any one of embodiments 87-91, wherein the second multi-component pharmaceutical composition comprises any one of the multi-component pharmaceutical compositions of embodiments 1-12, 15-30, 32-53, 55-64, and 66-86.

Embodiment 93. The method of any one of embodiments 87-92, wherein the first multi-component pharmaceutical composition comprises any one of the multi-component pharmaceutical compositions of embodiments 1-12, 15-30, 32-53, 55-64, and 66-86, and the second multi-component pharmaceutical composition comprises any one of the multi-component pharmaceutical compositions of embodiments 1-12, 15-30, 32-53, 55-64, and 66-86 other than the first multi-component pharmaceutical composition.

Embodiment 94. The method of any one of embodiments 87-93, wherein all of the three or more first components is different than all of the three or more second components.

Embodiment 95. A method for administering multi-component pharmaceutical compositions to a human or animal patient in need thereof, comprising:
administering to the patient a first multi-component pharmaceutical composition consisting essentially of three or more first components at a first time of day;
administering to the patient a second multi-component pharmaceutical composition consisting essentially of three or more second components at a second time of day, wherein at least one of the first components is different than at least one of the second components; and
administering to the patient a third multi-component pharmaceutical composition consisting essentially of three or more third components at a third time of day, wherein at least one of the third components is different than at least one of the first components and at least one of the second components.

Embodiment 96. The method of embodiment 95, wherein each of the first components is different than each of the second components and each of the third components; and
wherein each of the second components is different than each of the third components.

Embodiment 97. A method for administering multi-component pharmaceutical compositions to a human or animal patient in need thereof, comprising:
administering to the patient a first multi-component pharmaceutical composition consisting essentially of first components at a first time of day;
administering to the patient a second multi-component pharmaceutical composition consisting essentially of second components at a second time of day, wherein each of the first components is different than each of the second components; and
administering to the patient a third multi-component pharmaceutical composition consisting essentially of third components at a third time of day, wherein each of the third components is different than each of the first components and each of the second components.

Embodiment 98. The method of embodiment 97, wherein the first multi-component pharmaceutical composition consists essentially of two, three, four, five, six, seven, eight, nine, ten, eleven, twelve, fifteen, twenty, twenty-five, or thirty first components.

Embodiment 99. The method of any one of embodiments 97-98, wherein the second multi-component pharmaceutical composition consists essentially of two, three, four, five, six, seven, eight, nine, ten, eleven, twelve, fifteen, twenty, twenty-five, or thirty second components.

Embodiment 100. The method of any one of embodiments 97-99, wherein the third multi-component pharmaceutical composition consists essentially of two, three, four, five, six, seven, eight, nine, ten, eleven, twelve, fifteen, twenty, twenty-five, or thirty third components.

Embodiment 101. The method of any one of embodiments 97-100, wherein the first components are chosen from:
alfalfa, barley grass, blessed thistle, cauliflower, *chlorella*, cilantro, dandelion, flax seed, Japanese knotweed, kelp, lemon balm, lemon grass, nettle, plantain, sunflower seed, Siberian eleuthero, wheat grass, *spirulina*, blue green algae extract, açai, apple, asparagus, banana, beet, blueberry, broccoli, brussels sprout, cabbage, carrot, cranberry, cucumber, grape, grapefruit, hawthorn berry, lemon, lime, orange, pea, pear, pineapple, plum, pomegranate, pumpkin, raspberry, spinach, strawberry, tangerine, tart cherry, tomato, alpha galactosidase, amylase, bromelain, cellulase, coenzyme Q10, invertase, lactase, lipase, papain, peptidases, protease I, protease II, agarikon (laricifomes *officinalis* and fomitopsis *officinalis*), chaga (inonotus obliquus), enokitake (flammulina velutipes), himematsutake (*agaricus brasiliensis, agaricus* blazei), kawaratake (*trametes versicolor*), maitake (grifola *frondosa*), mesima (*phellinus* linteus), oyster hirotaka (*pleurotus* ostreatus), reishi (*Ganoderma lucidum*), shiitake (*lentinula edodes*), yamabushitake (hericium *erinaceus*), Zhu Ling (grifola *umbellata*), betaine HCl, choline, eriocitrin, fructose diphosphate (FDP), hesperidin, inositol, naringin, narirutin, resveratrol, rutin, lutein, calcium, copper, iodine, iron, magnesium, manganese, molybdenum, potassium, selenium, sodium, and zinc, vitamin A (as beta carotene and/or retinyl acetate, for example), vitamin B3 (niacin, nicotinamide, and/or nicotinamide riboside), vitamin B6, vitamin B12, vitamin C, vitamin D3, vitamin E, vitamin K1, riboflavin, biotin, folic acid, pantothenic acid, thiamine and mixtures of two or more of any of the foregoing.

Embodiment 102. The method of any one of embodiments 97-101, wherein the second components are chosen from:

alfalfa, barley grass, blessed thistle, cauliflower, *chlorella*, cilantro, dandelion, flax seed, Japanese knotweed, kelp, lemon balm, lemon grass, nettle, plantain, sunflower seed, Siberian eleuthero, wheat grass, *spirulina*, blue green algae extract, açai, apple, asparagus, banana, beet, blueberry, broccoli, brussels sprout, cabbage, carrot, cranberry, cucumber, grape, grapefruit, hawthorn berry, lemon, lime, orange, pea, pear, pineapple, plum, pomegranate, pumpkin, raspberry, spinach, strawberry, tangerine, tart cherry, tomato, alpha galactosidase, amylase, bromelain, cellulase, coenzyme Q10, invertase, lactase, lipase, papain, peptidases, protease I, protease II, agarikon (laricifomes *officinalis* and fomitopsis *officinalis*), chaga (inonotus obliquus), enokitake (flammulina velutipes), himematsutake (*agaricus brasiliensis, agaricus* blazei), kawaratake (*trametes versicolor*), maitake (grifola *frondosa*), mesima (*phellinus* linteus), oyster hirotaka (*pleurotus* ostreatus), reishi (*Ganoderma lucidum*), shiitake (*lentinula edodes*), yamabushitake (hericium *erinaceus*), Zhu Ling (grifola *umbellata*), betaine HCl, choline, eriocitrin, fructose diphosphate (FDP), hesperidin, inositol, naringin, narirutin, resveratrol, rutin, lutein, calcium, copper, iodine, iron, magnesium, manganese, molybdenum, potassium, selenium, sodium, and zinc, vitamin A (as beta carotene and/or retinyl acetate, for example), vitamin B3 (niacin, nicotinamide, and/or nicotinamide riboside), vitamin B6, vitamin B12, vitamin C, vitamin D3, vitamin E, vitamin K1, riboflavin, biotin, folic acid, pantothenic acid, thiamine and mixtures of two or more of any of the foregoing.

Embodiment 103. The method of any one of embodiments 97-102, wherein the third components are chosen from:

alfalfa, barley grass, blessed thistle, cauliflower, *chlorella*, cilantro, dandelion, flax seed, Japanese knotweed, kelp, lemon balm, lemon grass, nettle, plantain, sunflower seed, Siberian eleuthero, wheat grass, *spirulina*, blue green algae extract, açai, apple, asparagus, banana, beet, blueberry, broccoli, brussels sprout, cabbage, carrot, cranberry, cucumber, grape, grapefruit, hawthorn berry, lemon, lime, orange, pea, pear, pineapple, plum, pomegranate, pumpkin, raspberry, spinach, strawberry, tangerine, tart cherry, tomato, alpha galactosidase, amylase, bromelain, cellulase, coenzyme Q10, invertase, lactase, lipase, papain, peptidases, protease I, protease II, agarikon (laricifomes *officinalis* and fomitopsis *officinalis*), chaga (inonotus obliquus), enokitake (flammulina velutipes), himematsutake (*agaricus brasiliensis, agaricus* blazei), kawaratake (*trametes versicolor*), maitake (grifola *frondosa*), mesima (*phellinus* linteus), oyster hirotaka (*pleurotus* ostreatus), reishi (*Ganoderma lucidum*), shiitake (*lentinula edodes*), yamabushitake (hericium *erinaceus*), Zhu Ling (grifola *umbellata*), betaine HCl, choline, eriocitrin, fructose diphosphate (FDP), hesperidin, inositol, naringin, narirutin, resveratrol, rutin, lutein, calcium, copper, iodine, iron, magnesium, manganese, molybdenum, potassium, selenium, sodium, and zinc, vitamin A (as beta carotene and/or retinyl acetate, for example), vitamin B3 (niacin, nicotinamide, and/or nicotinamide riboside), vitamin B6, vitamin B12, vitamin C, vitamin D3, vitamin E, vitamin K1, riboflavin, biotin, folic acid, pantothenic acid, thiamine and mixtures of two or more of any of the foregoing.

Embodiment 104. A multi-component pharmaceutical composition consisting essentially of ten components.

Embodiment 105. The multi-component pharmaceutical composition of embodiment 104, wherein one of the ten components comprises methylsulfonylmethane.

Embodiment 106. The multi-component pharmaceutical composition of embodiment 104, comprising:
(a) methylsulfonylmethane; (b) one or more of vitamin B3 and rutin; and (c) selenium, zinc, garlic, *ginseng*, probiotics, astralagus, *echinacea*, olive leaf, ashwagandha, rutin, vitamin A, vitamin C, vitamin E, folic acid, vitamin B6, vitamin B12, phenols, flavones, phytosterols, curcumin, blueberry, lipoic acid, resveratrol, green tea, vitamin D, docosahexanoic acid (DHA), eicosapentaenoic acid (EPA), pomegranate, quercetin, cocoa, catechins, anthocyanins, purple grape products, red wine extract, cranberry, flavonoids, and flavonols.

Embodiment 107. The multi-component pharmaceutical composition of any one of embodiments 104-106, wherein the ten components are chosen from alfalfa, barley grass, blessed thistle, cauliflower, *chlorella*, cilantro, dandelion, flax seed, Japanese knotweed, kelp, lemon balm, lemon grass, nettle, plantain, sunflower seed, Siberian eleuthero, wheat grass, *spirulina*, blue green algae extract, açai, apple, asparagus, banana, beet, blueberry, broccoli, brussels sprout, cabbage, carrot, cranberry, cucumber, grape, grapefruit, hawthorn berry, lemon, lime, orange, pea, pear, pineapple, plum, pomegranate, pumpkin, raspberry, spinach, strawberry, tangerine, tart cherry, tomato, alpha galactosidase, amylase, bromelain, cellulase, coenzyme Q10, invertase, lactase, lipase, papain, peptidases, protease I, protease II, agarikon (laricifomes *officinalis* and fomitopsis *officinalis*), chaga (inonotus obliquus), enokitake (flammulina velutipes), himematsutake (*agaricus brasiliensis, agaricus* blazei), kawaratake (*trametes versicolor*), maitake (grifola *frondosa*), mesima (*phellinus* linteus), oyster hirotaka (*pleurotus* ostreatus), reishi (*Ganoderma lucidum*), shiitake (*lentinula edodes*), yamabushitake (hericium *erinaceus*), Zhu Ling (grifola *umbellata*), betaine HCl, choline, eriocitrin, fructose diphosphate (FDP), hesperidin, inositol, naringin, narirutin, resveratrol, rutin, lutein, calcium, copper, iodine, iron, magnesium, manganese, molybdenum, potassium, selenium, sodium, and zinc, vitamin A (as beta carotene and/or retinyl acetate, for example), vitamin B3 (niacin, nicotinamide, and/or nicotinamide riboside), vitamin B6, vitamin B12, vitamin C, vitamin D3, vitamin E, vitamin K1, riboflavin, biotin, folic acid, pantothenic acid, and thiamine.

Embodiment 108. A collection of three multi-component pharmaceutical compositions, consisting of:
a first pharmaceutical composition consisting essentially of ten first components;
a second pharmaceutical composition consisting essentially of ten second components, wherein at least one of the ten first components is different than at least one of the ten second components; and
a third pharmaceutical composition consisting essentially of ten third components, wherein at least one of the ten third components is different than at least one of the ten first components and at least one of the ten second components.

Embodiment 109. The collection of embodiment 108, wherein the first pharmaceutical composition, the second pharmaceutical composition, and the third pharmaceutical composition each comprise methylsulfonylmethane.

Embodiment 110. The collection of embodiment 108, wherein at least one of the first pharmaceutical composition, the second pharmaceutical composition, and the third pharmaceutical composition comprises:

(a) methylsulfonylmethane; (b) one or more of vitamin B3, fructose 1,6-diphosphate, and rutin; and (c) selenium, zinc, garlic, *ginseng*, probiotics, astralagus, *echinacea*, olive leaf, ashwagandha, rutin, vitamin A, vitamin C, vitamin E, folic acid, vitamin B6, vitamin B12, phenols, flavones, phytosterols, curcumin, blueberry, lipoic acid, resveratrol, green tea, vitamin D, docosahexanoic acid (DHA), eicosapentaenoic acid (EPA), pomegranate, quercetin, cocoa, catechins, anthocyanins, purple grape products, red wine extract, cranberry, flavonoids, and flavonols, for a total of ten components.

Embodiment 111. The collection of embodiment 108, wherein the first pharmaceutical composition, the second pharmaceutical composition, and the third pharmaceutical composition each consists essentially of (a) methylsulfonylmethane; (b) one or more of vitamin B3 and rutin; and (c) selenium, zinc, garlic, *ginseng*, probiotics, astralagus, *echinacea*, olive leaf, ashwagandha, rutin, vitamin A, vitamin C, vitamin E, folic acid, vitamin B6, vitamin B12, phenols, flavones, phytosterols, curcumin, blueberry, lipoic acid, resveratrol, green tea, vitamin D, docosahexanoic acid (DHA), eicosapentaenoic acid (EPA), pomegranate, quercetin, cocoa, catechins, anthocyanins, purple grape products, red wine extract, cranberry, flavonoids, and flavonols, for a total of ten components;

wherein the first pharmaceutical composition differs from the second pharmaceutical composition and the third pharmaceutical composition by at least one first component; and the second pharmaceutical composition differs from the third pharmaceutical composition by at least one second component.

Embodiment 112. A collection of three multi-component pharmaceutical compositions, consisting of:

a first pharmaceutical composition consisting essentially of first components;

a second pharmaceutical composition consisting essentially of second components, wherein each of the first components is different than each of the second components; and a third pharmaceutical composition consisting essentially of third components, wherein each of the third components is different than each of the first components and each of the second components.

Embodiment 113. The collection of embodiment 112, wherein the first components are chosen from alfalfa, barley grass, blessed thistle, cauliflower, *chlorella*, cilantro, dandelion, flax seed, Japanese knotweed, kelp, lemon balm, lemon grass, nettle, plantain, sunflower seed, Siberian eleuthero, wheat grass, *spirulina*, blue green algae extract, açai, apple, asparagus, banana, beet, blueberry, broccoli, brussels sprout, cabbage, carrot, cranberry, cucumber, grape, grapefruit, hawthorn berry, lemon, lime, orange, pea, pear, pineapple, plum, pomegranate, pumpkin, raspberry, spinach, strawberry, tangerine, tart cherry, tomato, alpha galactosidase, amylase, bromelain, cellulase, coenzyme Q10, invertase, lactase, lipase, papain, peptidases, protease I, protease II, agarikon (laricifomes *officinalis* and fomitopsis *officinalis*), chaga (inonotus obliquus), enokitake (flammulina velutipes), himematsutake (*agaricus brasiliensis, agaricus* blazei), kawaratake (*trametes versicolor*), maitake (grifola *frondosa*), mesima (*phellinus* linteus), oyster hirotaka (*pleurotus* ostreatus), reishi (*Ganoderma lucidum*), shiitake (*lentinula edodes*), yamabushitake (hericium *erinaceus*), Zhu Ling (grifola *umbellata*), betaine HCl, choline, eriocitrin, fructose diphosphate (FDP), hesperidin, inositol, naringin, narirutin, resveratrol, rutin, lutein, calcium, copper, iodine, iron, magnesium, manganese, molybdenum, potassium, selenium, sodium, and zinc, vitamin A (as beta carotene and/or retinyl acetate, for example), vitamin B3 (niacin, nicotinamide, and/or nicotinamide riboside), vitamin B6, vitamin B12, vitamin C, vitamin D3, vitamin E, vitamin K1, riboflavin, biotin, folic acid, pantothenic acid, thiamine and mixtures of two or more of any of the foregoing.

Embodiment 114. The collection of any one of embodiments 112-113, wherein the second components are chosen from alfalfa, barley grass, blessed thistle, cauliflower, *chlorella*, cilantro, dandelion, flax seed, Japanese knotweed, kelp, lemon balm, lemon grass, nettle, plantain, sunflower seed, Siberian eleuthero, wheat grass, *spirulina*, blue green algae extract, açai, apple, asparagus, banana, beet, blueberry, broccoli, brussels sprout, cabbage, carrot, cranberry, cucumber, grape, grapefruit, hawthorn berry, lemon, lime, orange, pea, pear, pineapple, plum, pomegranate, pumpkin, raspberry, spinach, strawberry, tangerine, tart cherry, tomato, alpha galactosidase, amylase, bromelain, cellulase, coenzyme Q10, invertase, lactase, lipase, papain, peptidases, protease I, protease II, agarikon (laricifomes *officinalis* and fomitopsis *officinalis*), chaga (inonotus obliquus), enokitake (flammulina velutipes), himematsutake (*agaricus brasiliensis, agaricus* blazei), kawaratake (*trametes versicolor*), maitake (grifola *frondosa*), mesima (*phellinus* linteus), oyster hirotaka (*pleurotus* ostreatus), reishi (*Ganoderma lucidum*), shiitake (*lentinula edodes*), yamabushitake (hericium *erinaceus*), Zhu Ling (grifola *umbellata*), betaine HCl, choline, eriocitrin, fructose diphosphate (FDP), hesperidin, inositol, naringin, narirutin, resveratrol, rutin, lutein, calcium, copper, iodine, iron, magnesium, manganese, molybdenum, potassium, selenium, sodium, and zinc, vitamin A (as beta carotene and/or retinyl acetate, for example), vitamin B3 (niacin, nicotinamide, and/or nicotinamide riboside), vitamin B6, vitamin B12, vitamin C, vitamin D3, vitamin E, vitamin K1, riboflavin, biotin, folic acid, pantothenic acid, thiamine and mixtures of two or more of any of the foregoing.

Embodiment 115. The collection of any one of embodiments 112-114, wherein the third components are chosen from alfalfa, barley grass, blessed thistle, cauliflower, *chlorella*, cilantro, dandelion, flax seed, Japanese knotweed, kelp, lemon balm, lemon grass, nettle, plantain, sunflower seed, Siberian eleuthero, wheat grass, *spirulina*, blue green algae extract, açai, apple, asparagus, banana, beet, blueberry, broccoli, brussels sprout, cabbage, carrot, cranberry, cucumber, grape, grapefruit, hawthorn berry, lemon, lime, orange, pea, pear, pineapple, plum, pomegranate, pumpkin, raspberry, spinach, strawberry, tangerine, tart cherry, tomato, alpha galactosidase, amylase, bromelain, cellulase, coenzyme Q10, invertase, lactase, lipase, papain, peptidases, protease I, protease II, agarikon (laricifomes *officinalis* and fomitopsis *officinalis*), chaga (inonotus obliquus), enokitake (flammulina velutipes), himematsutake (*agaricus brasiliensis, agaricus blazei*), kawaratake (*trametes versicolor*), maitake (grifola *frondosa*), mesima (*phellinus* linteus), oyster hirotaka (*pleurotus* ostreatus), reishi (*Ganoderma lucidum*), shiitake (*lentinula edodes*), yamabushitake (hericium *erinaceus*), Zhu Ling (grifola *umbellata*), betaine HCl, choline, eriocitrin, fructose diphosphate (FDP), hesperidin, inositol, naringin, narirutin, resveratrol, rutin, lutein, calcium, copper, iodine, iron, magnesium, manganese, molybdenum, potassium, selenium, sodium, and zinc, vitamin A (as beta carotene and/or retinyl acetate, for example), vitamin B3 (niacin, nicotinamide, and/or nicotinamide riboside), vitamin B6, vitamin B12, vitamin C, vitamin D3, vitamin E, vitamin K1, riboflavin, biotin, folic acid, pantothenic acid, thiamine and mixtures of two or more of any of the foregoing.

Embodiment 116. The collection of any one of embodiments 112-115, comprising no more than two, three, four, five, six, seven, eight, nine, ten, eleven, twelve, fifteen, twenty, twenty-five, or thirty first components.

Embodiment 117. The collection of any one of embodiments 112-116, comprising no more than two, three, four, five, six, seven, eight, nine, ten, eleven, twelve, fifteen, twenty, twenty-five, or thirty second components.

Embodiment 118. The collection of any one of embodiments 112-117, comprising no more than two, three, four, five, six, seven, eight, nine, ten, eleven, twelve, fifteen, twenty, twenty-five, or thirty third components.

As previously stated, detailed embodiments of the present invention are disclosed herein; however, it is to be understood that the disclosed embodiments are merely exemplary of the invention that may be embodied in various forms. The scope and intent of this specification include all modifications, variations, and changes, in detail and otherwise, which can be made to such specification. It is intended that this specification be interpreted as illustrative rather than limiting. It will be appreciated that many modifications and other variations stand within the intended scope of this invention as claimed below. Furthermore, the foregoing description of various embodiments does not necessarily imply exclusion. For example, "some" embodiments may include all or part of "other" and "further" embodiments within the scope of this invention. In addition, "a" does not mean "one and only one;" "a" can mean "one and more than one."

I claim:

1. A multi-component pharmaceutical composition consisting essentially of:
   methylsulfonylmethane (MSM) in an amount of at least 10% by weight;
   fructose diphosphate (FDP) of at least 20% by weight; and
   a third component chosen from one of docosahexanoic acid (DHA), resveratrol, blueberry, and curcumin.

2. The multi-component pharmaceutical composition of claim 1, wherein the
   methylsulfonylmethane (MSM) is present in an amount ranging from at least 10% to about 90% by weight.

3. The multi-component pharmaceutical composition of claim 1, wherein the methylsulfonylmethane (MSM) is present in an amount of no more than 50% by weight.

4. The multi-component pharmaceutical composition of claim 1, wherein the
   fructose diphosphate (FDP) is present in an amount of no more than 90% by weight.

5. The multi-component pharmaceutical composition of claim 1, wherein the
   fructose diphosphate (FDP) is present in an amount of at least 50% by weight.

6. The multi-component pharmaceutical composition of claim 1, wherein the
   fructose diphosphate (FDP) is present in an amount of no more than 50% by weight.

7. The multi-component pharmaceutical composition of claim 1, wherein the
   third component is present in an amount ranging from 0.01% to 90% by weight.

8. A multi-component pharmaceutical composition consisting essentially of:
   methylsulfonylmethane (MSM) in an amount of at least 10% by weight;
   fructose diphosphate (FDP) in an amount of at least 20% by weight; and
   an herbal component or a nutritional component;
   wherein the composition does not contain docosahexanoic acid (DHA), resveratrol, blueberry, curcumin, trehalose, green tea extract, ashwagandha, or rutin.

9. The multi-component pharmaceutical composition of claim 8, wherein the
   methylsulfonylmethane (MSM) is present in an amount ranging from at least 10% to 90% by weight.

10. The multi-component pharmaceutical composition of claim 8, wherein
    the methylsulfonylmethane (MSM) is present in an amount of at least 20% by weight.

11. The multi-component pharmaceutical composition of claim 8, wherein
    the methylsulfonylmethane (MSM) is present in an amount of no more than 50% by weight.

12. The multi-component pharmaceutical composition of claim 8, wherein
    the fructose diphosphate (FDP) is present in an amount ranging from at least 20% to 90% by weight.

13. The multi-component pharmaceutical composition of claim 8, wherein
    the fructose diphosphate (FDP) is present in an amount of at least about 50% by weight.

14. The multi-component pharmaceutical composition of claim 8, wherein
    the herbal component or the nutritional component is present in an amount ranging from 0.01% to 90% by weight.

15. The multi-component pharmaceutical composition of claim 8, wherein
    the herbal component or the nutritional component is present in an amount of at least 5% by weight.

* * * * *